United States Patent [19]

Hayashi et al.

[11] 4,278,688
[45] Jul. 14, 1981

[54] PROSTAGLANDIN ANALOGUES

[75] Inventors: Masaki Hayashi; Katsuichi Shimoji, both of Takatsuki; Yoshinobu Arai, Toyonaka, all of Japan

[73] Assignee: Ono Pharmaceutical Co., Osaka, Japan

[21] Appl. No.: 112,676

[22] Filed: Jan. 16, 1980

Related U.S. Application Data

[62] Division of Ser. No. 940,685, Sep. 9, 1978, Pat. No. 4,215,142.

[30] Foreign Application Priority Data

Sep. 16, 1977 [JP] Japan .................. 52-110504

[51] Int. Cl.$^3$ .................. A61K 31/557; C07C 177/00
[52] U.S. Cl. .......................... 424/305; 210/410.9 R; 210/413; 536/103; 542/426; 560/53; 560/118; 560/121; 562/463; 562/500; 562/503; 424/308; 424/317
[58] Field of Search .................. 560/121; 562/503; 424/305, 317; 200/410.9 R, 413

[56] References Cited

U.S. PATENT DOCUMENTS 4,171,447  10/1979  Smith .................. 560/121

Primary Examiner—Robert Gerstl
Attorney, Agent, or Firm—Stephen I. Miller

[57] ABSTRACT

Prostaglandin $E_1$ analogues of the general formula:

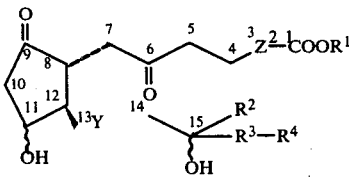

IV

[wherein Y represents ethylene or trans-vinylene, Z represents ethylene or trans-vinylene, $R^1$ represents a hydrogen atom, an alkyl group containing 1 to 12 carbon atoms, an aralkyl group containing from 7 to 12 carbon atoms, a cycloalkyl group containing from 4 to 7 carbon atoms and unsubstituted or substituted by at least one alkyl group containing from 1 to 6 carbon atoms, a phenyl group unsubstituted or substituted by at least one chlorine atom, trifluoromethyl group, alkyl group containing from 1 to 4 carbon atoms or phenyl group, a —$C_mH_{2m}COOR^5$ group (wherein m represents an integer of from 1 to 12 and $R^5$ represents a hydrogen atom or an alkyl group containing from 1 to 4 carbon atoms ), a —$C_nH_{2n}OR^6$ group (wherein $R^6$ represents a hydrogen atom or an alkyl group containing from 1 to 4 carbon atoms and n represents an integer of from 2 to 12), or a

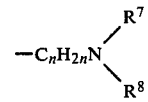

group (wherein $R^7$ and $R^8$ each represent a hydrogen atom or an alkyl group containing from 1 to 4 carbon atoms and n is as hereinbefore defined), $R^2$ represents a hydrogen atom or a methyl or ethyl group, $R^3$ represents a single bond or an alkylene group containing from 1 to 4 carbon atoms, $R^4$ represents a hydrogen atom, an alkyl group containing from 1 to 8 carbon atoms, a cycloalkyl group containing from 4 to 7 carbon atoms and unsubstituted or substituted by at least one alkyl group containing from 1 to 8 carbon atoms, or represents a phenyl or phenoxy group unsubstituted or substituted by at least one chlorine atom, trifluoromethyl group or alkyl group containing from 1 to 3 carbon atoms, and the wavy line attached to the C-11 and C-15 carbon atoms represents α- or β-configuration or mixtures thereof] and cyclodextrin clathrates thereof, and, when $R^1$ represents a hydrogen atom or a group $C_mH_{2m}COOR^5$ in which $R^5$ represents a hydrogen atom, non-toxic salts thereof and, when $R^1$ represents a group

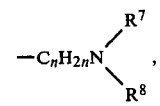

, non-toxic acid addition salts thereof, are new compounds and possess characteristic prostaglandin-like properties.

8 Claims, No Drawings

PROSTAGLANDIN ANALOGUES

This is a division of application Ser. No. 940,685 filed Sept. 9, 1978, now U.S. Pat. No. 4,215,142.

This invention is concerned with new prostaglandin analogues.

Prostaglandins are derivatives of prostanoic acid which has the following formula:

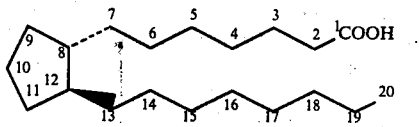

Various types of prostaglandins are known, the types depending inter alia on the structure and substituents on the alicyclic ring. For example, the alicyclic ring of prostaglandin E(PGE) has the structure:

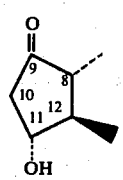

The dotted lines in the foregoing formulae and in other formulae throughout this specification denote, in accordance with generally accepted rules of nomenclature, that the attached grouping lies behind the general plane of the ring system, i.e. that the grouping is in α-configuration, the thickened lines denote that the grouping lies in front of the general plane of the system, i.e. that the grouping is in β-configuration, and the wavy line ∿ indicates that the grouping is in α- or β-configuration.

Such compounds are sub-classified according to the position of double bond(s) in the side chain(s) attached to the 8- and 12-positions of the alicyclic ring. Thus $PG_1$ compounds have a trans-double bond between $C_{13}$–$C_{14}$(trans-$\Delta^{13}$) and $PG_2$ compounds have a cis-double bond between $C_5$–$C_6$ and a trans-double bond between $C_{13}$–$C_{14}$(cis-$\Delta^5$, trans-$\Delta^{13}$). For example, prostaglandin $E_1$ ($PGE_1$) is characterised by the following structure III.

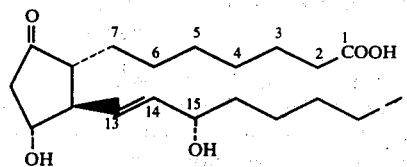

The structure of $PGE_2$, as a member of the $PG_2$ group, corresponds to that of Formula III with a cis-double bond between the carbon atoms in positions 5 and 6. Compounds in which the double bond between the carbon atoms in positions 13 and 14 of members of the $PG_1$ group is replaced by ethylene are known as dihydroprostaglandins, e.g. dihydro-prostaglandin-$E_1$ (dihydro-$PGE_1$).

Moreover, when one or more methylene groups are eliminated from the aliphatic group attached to the 12-position of the alicyclic ring of the prostaglandins the compounds are known, in accordance with the usual rules of organic nomenclature, as nor-prostaglandins and, when more than one methylene group is eliminated, the number is indicated by di-, tri- etc. before the prefix "nor".

Prostaglandins are generally known to possess pharmacological properties, for example they stimulate smooth muscle, have hypotensive, diuretic, bronchodilating and antilipolytic activities, and also inhibit blood platelet aggregation and gastric acid secretion, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. They are fat-soluble substances obtainable in very small quantities from various tissues of animals which secrete the prostaglandins in the living body.

For example, PGE's have an inhibiting effect on gastric acid secretion and may, accordingly, be used in the treatment of gastric ulcers. They also inhibit the release of free fatty acid induced by epinephrine and as a result they reduce the concentration of free fatty acid in blood, and are, accordingly, useful in the prevention of arteriosclerosis and hyperlipemia. $PGE_1$ inhibits blood platelet aggregation and also removes the thrombus and prevents thrombosis. PGE's have a stimulating effect on smooth muscle and increase the intestinal peristalsis; these actions indicate therapeutic utility on post-operative ileus and as purgatives. PGE's may also be used as oxytocics, as abortifacients in the first and second trimesters; in the post-labour abortion of the placenta, and as oral contraceptives because they regulate the sexual cycle of female mammals. PGE's have vasodilator and diuretic activities. They are useful for improvement in patients suffering from cerebral vascular disease because they increase the cerebral blood flow, and are also useful in the treatment of asthmatic conditions in patients because of their bronchodilating activity.

During the past decade widespread investigations have been carried out in order to discover inter alia new products possessing the pharmacological properties of the 'natural' prostaglandins or one or more of such properties to an enhanced degree, or hitherto unknown pharmacological properties. It has now been found, after research and experimentation, that by replacing the hydrogen atoms attached to the C-6 carbon atom of prostaglandin $E_1$ and certain analogues thereof by an oxo group (i.e. =O), new prostaglandin $E_1$ analogues are obtained which possess the pharmacological properties of the 'natural' prostaglandins and are, in some aspects of their activities, an improvement, for example possessing an enhanced strength for activity and/or a prolonged duration of activity.

The present invention accordingly provides the new prostaglandin $E_1$ analogues of the general formula:

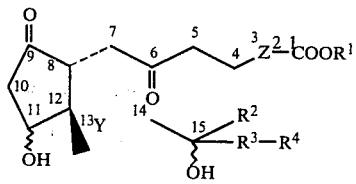

[wherein Y represents ethylene (i.e. —CH$_2$—CH$_2$—) or, preferably, trans-vinylene (i.e.

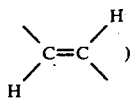
)

Z represents ethylene or trans-vinylene, $R^1$ represents a hydrogen atom, a straight- or branched-chain alkyl group containing from 1 to 12 carbon atoms, an aralkyl group containing from 7 to 12 carbon atoms, a cycloalkyl group containing from 4 to 7 carbon atoms in the ring and unsubstituted or substituted by at least one straight- or branched-chain alkyl group containing from 1 to 6 carbon atoms, a phenyl group unsubstituted or substituted by at least one chlorine atom, trifluoromethyl group, straight- or branched-chain alkyl group containing from 1 to 4 carbon atoms or phenyl group, a —$C_mH_{2m}COOR^5$ group (wherein m represents an integer of from 1 to 12 and $R^5$ represents a hydrogen atom or a straight- or branched-chain alkyl group containing from 1 to 4 carbon atoms), a —$C_nH_{2n}OR^6$ group (wherein $R^6$ represents a hydrogen atom or a straight- or branched-chain alkyl group containing from 1 to 4 carbon atoms and n represents an integer of from 2 to 12), or a

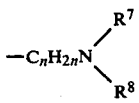

group (wherein $R^7$ and $R^8$, which may be the same or different, each represent a hydrogen atom or a straight- or branched-chain alkyl group containing from 1 to 4 carbon atoms and n is as hereinbefore defined), $R^2$ represents a hydrogen atom or a methyl or ethyl group, $R^3$ represents a single bond or a straight- or branched-chain alkylene group containing from 1 to 4 carbon atoms, $R^4$ represents a hydrogen atom, a straight- or branched-chain alkyl group containing from 1 to 8 carbon atoms, a cycloalkyl group containing from 4 to 7 carbon atoms in the ring and unsubstituted or substituted by at least one straight- or branched-chain alkyl group containing from 1 to 8 carbon atoms, or represents a phenyl or phenoxy group unsubstituted or substituted by at least one chlorine atom, trifluoromethyl group or alkyl group containing from 1 to 3 carbon atoms, and the wavy line attached to the C-11 and C-15 carbon atoms represents α- or β-configuration (i.e. S- or R-configuration) or mixtures thereof] and cyclodextrin clathrates of such acids and esters and, when $R^1$ represents a hydrogen atom or a group —$C_mH_{2m}COOR^5$ in which $R^5$ represents a hydrogen atom and m is as hereinbefore defined, non-toxic (e.g. sodium) salts thereof and, when $R^1$ represents a group

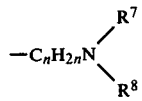

in which n, $R^7$ and $R^8$ are as hereinbefore defined, non-toxic acid addition salts thereof. Preferably the hydroxy groups attached to the C-11 and C-15 carbon atoms of formula IV are in α-configuration.

The present invention is concerned with all compounds of general formula IV in the 'natural' form or its enantiomeric form, or mixtures thereof, more particularly the racemic form consisting of equimolecular mixtures of natural and its enantiomeric form.

As will be apparent to those skilled in the art, the compounds depicted in general formula IV have at least four centres of chirality, these four centres of chirality being at the C-8, C-11, C-12 and C-15 carbon atoms. Still further centres of chirality occur when $R^1$ or $R^4$ is a branched-chain alkyl group, or $R^3$ is a branched-chain alkylene group. The presence of chirality leads, as is well known, to the existence of isomerism. However, the compounds of general formula IV all have such a configuration that the side-chains attached to the ring carbon atoms in the positions identified as 8 and 12 are trans with respect to each other. Accordingly, all isomers of general formula IV, and mixtures thereof, which have those side-chains attached to the ring carbon atoms in positions 8 and 12 in the trans configuration and have hydroxy groups as depicted in the 11- and 15-positions are to be considered within the scope of formula IV.

Examples of the straight- or branched-chain alkyl group containing from 1 to 12 carbon atoms represented by $R^1$ are methyl, ethyl, propyl, butyl, pentyl, hexyl, heptyl, octyl, nonyl, decyl, undecyl and dodecyl and their isomers.

Examples of the aralkyl group containing from 7 to 12 carbon atoms represented by $R^1$ are benzyl, 1-phenylethyl, 2-phenylethyl, 3-phenylbutyl, 4-phenylbutyl, 1-(2-naphthyl)ethyl and 2-(1-naphthyl)ethyl.

Examples of the cycloalkyl group containing from 4 to 7 carbon atoms unsubstituted or substituted by at least one alkyl group containing from 1 to 6 carbon atoms represented by $R^1$ are 1-propylcyclobutyl, 1-butylcyclobutyl, 1-pentylcyclobutyl, 1-hexylcyclobutyl, 2-methylcyclobutyl, 2-propylcyclobutyl, 3-ethylcyclobutyl, 3-propylcyclobutyl, 2,3,4-triethylcyclobutyl, cyclopentyl, 3-ethylcyclopentyl, 3-propylcyclopentyl, 3-butylcyclopentyl, 3-tert-butylcyclopentyl, 2,2-dimethylcyclopentyl, 1-methyl-3-propylcyclopentyl, 2-methyl-3-propylcyclopentyl, 2-methyl-4-propylcyclopentyl, cyclohexyl, 3-ethylcyclohexyl, 3-isopropylcyclohexyl, 4-methylcyclohexyl, 4-ethylcyclohexyl, 4-propylcyclohexyl, 4-tert-butylcyclohexyl, 2,2-dimethylcyclohexyl, 2,6-dimethylcyclohexyl, 2,6-dimethyl-4-propylcyclohexyl and cycloheptyl.

Examples of the phenyl group unsubstituted or substituted by at least one chlorine atom, trifluoromethyl group, straight- or branched-chain alkyl group containing from 1 to 4 carbon atoms or phenyl group represented by $R^1$ are phenyl, 2-chlorophenyl, 3-chlorophenyl, 4-chlorophenyl, 2,4-dichlorophenyl, 2,4,6-trichlorophenyl, 2-tolyl, 3-tolyl, 4-tolyl, 4-ethylphenyl, 4-tert-butylphenyl, 4-sec-butylphenyl, 3-trifluoromethylphenyl and 4-biphenyl.

Examples of the $C_mH_{2m}$ and $C_nH_{2n}$ moieties of the $C_mH_{2m}COOR^5$, —$C_nH_{2n}OR^6$ and

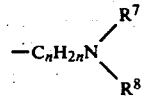

groups represented by $R^1$, are methylene (when m in the $C_mH_{2m}$ moiety is 1), ethylene, trimethylene, tetramethylene, pentamethylene, hexamethylene, heptamethylene, octamethylene, nonamethylene, decamethylene, undecamethylene, dodecamethylene and their isomers.

The straight- or branched-chain alkyl group containing from 1 to 4 carbon atoms represented by $R^5$, $R^6$, $R^7$ and $R^8$, may be methyl, ethyl, propyl, isopropyl, butyl, isobutyl, sec-butyl or tert-butyl.

Preferably $R^1$ represents a hydrogen atom or a straight- or branched-chain alkyl group containing from 1 to 4 carbon atoms, e.g. methyl.

$R^2$ preferably represents a hydrogen atom or methyl.

Preferably the grouping —$R^3$—$R^4$ represents pentyl, 1-methylpentyl, 2-methylpentyl, 3-methylpentyl, 4-methylpentyl, 1,1-dimethylpentyl, 1,2-dimethylpentyl, 1,4-dimethylpentyl, 1-ethylpentyl, 2-ethylpentyl, 1-propylpentyl, 2-propylpentyl, hexyl, 1-methylhexyl, 2-methylhexyl, 1,1-dimethylhexyl, 1-ethylhexyl, 2-ethylhexyl, heptyl, 2-methylheptyl, 2-ethylheptyl, nonyl, undecyl, cyclobutyl, 1-propylcyclobutyl, 1-butylcyclobutyl, 1-pentylcyclobutyl, 1-hexylcyclobutyl, 2-methylcyclobutyl, 2-propylcyclobutyl, 3-ethylcyclobutyl, 3-propylcyclobutyl, 2,3,4-triethylcyclobutyl, cyclopentyl, cyclopentylmethyl, 2-cyclopentylethyl, 1-cyclopentylethyl, 3-cyclopentylpropyl, 2-cyclopentylpropyl, 2-pentylcyclopentyl, 2,2-dimethylcyclopentyl, 3-ethylcyclopentyl, 3-propylcyclopentyl, 3-butylcyclopentyl, 3-tert-butylcyclopentyl, 1-methyl-3-propylcyclopentyl, 2-methyl-3-propylcyclopentyl, 2-methyl-4-propylcyclopentyl, cyclohexyl, cyclohexylmethyl, 2-cyclohexylethyl, 1-cyclohexylethyl, 3-cyclohexylpropyl, 1-methyl-2-cyclohexylethyl, 2-cyclohexylpropyl, 1-methyl-1-cyclohexylethyl, 4-cyclohexylbutyl, 3-ethylcyclohexyl, 3-isopropylcyclohexyl, 4-methylcyclohexyl, 4-ethylcyclohexyl, 4-propylcyclohexyl, 4-butylcyclohexyl, 4-tert-butylcyclohexyl, 2,6-dimethylcyclohexyl, 2,2-dimethylcyclohexyl, 2,6-dimethyl-4-propylcyclohexyl, 1-methylcyclohexylmethyl, cycloheptyl, cycloheptylmethyl, 2-cycloheptylethyl, 1-cycloheptylethyl, phenyl, benzyl, 1-phenylethyl, 2-phenylethyl, phenoxymethyl, (3-chlorophenoxy)methyl, (4-chlorophenoxy)methyl or (3-trifluoromethylphenoxy)methyl.

Preferably $R^3$ represents a single bond or a methylene group. Preferably $R^4$ represents an n-pentyl, n-hexyl or n-heptyl group unsubstituted or substituted by a methyl group, or represents a cyclopentyl or cyclohexyl group, unsubstituted or substituted by an alkyl group containing from 1 to 4 carbon atoms, or a phenoxy group unsubstituted or substituted by a chlorine atom.

Prostaglandin analogues of general formula IV wherein $R^4$ represents a cycloalkyl group containing from 4 to 7 carbon atoms in the ring and unsubstituted or substituted by at least one straight- or branched-chain alkyl group containing from 1 to 8 carbon atoms, for example a cyclopentyl or cyclohexyl group, unsubstituted or substituted by an alkyl group containing from 1 to 4 carbon atoms, are most preferred.

According to a feature of the present invention, the prostaglandin $E_1$ analogues of general formula IV, wherein $R^1$ represents a hydrogen atom or a straight- or branched-chain alkyl group containing from 1 to 12 carbon atoms and the other symbols are as hereinbefore defined, may be prepared by the hydrolysis to hydroxy groups of the groups $OR^9$ of a compound of the general formula:

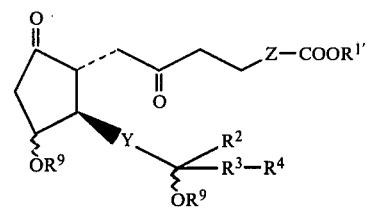

wherein $R^{1'}$ represents a hydrogen atom or a straight- or branched-chain alkyl group containing from 1 to 12 carbon atoms, $R^9$ represents a tetrahydropyran-2-yl or tetrahydrofuran-2-yl group, each such group being unsubstituted or substituted by at least one alkyl group, or represents a 1-ethoxyethyl group, and the other symbols are as hereinbefore defined.

The groups $OR^9$ of the compounds of general formula V may be converted to hydroxy groups by mild acidic hydrolysis (1) with an aqueous solution of an organic acid such as acetic acid, propionic acid, oxalic acid or p-toluenesulphonic acid, or an aqueous solution of an inorganic acid, such as hydrochloric acid or sulphuric acid, advantageously in the presence of an inert organic solvent miscible with water, e.g. a lower alkanol such as methanol or ethanol (preferably methanol), or an ether such as 1,2-dimethoxyethane, dioxan or tetrahydrofuran (preferably tetrahydrofuran), at a temperature ranging from ambient to 75° C. (preferably at a temperature below 45° C.), or (2) with an anhydrous solution of an organic acid such as p-toluenesulphonic acid or trifluoroacetic acid in a lower alkanol such as methanol or ethanol at a temperature ranging from 10° to 45° C. Advantageously the mild hydrolysis may be carried out with a mixture of hydrochloric acid, water and tetrahydrofuran, a mixture of hydrochloric acid, water and methanol, a mixture of acetic acid, water and tetrahydrofuran, or a mixture of p-toluenesulphonic acid and methanol.

Compounds of general formula V may be prepared by the oxidation of a compound of the general formula:

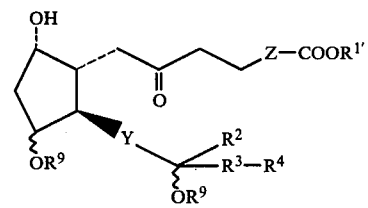

(wherein the various symbols are as hereinbefore defined), by methods known per se for the conversion of a hydroxy group in the 9-position of a prostaglandin compound to an oxo group. By the expression "methods known per se" as used in this specification is meant methods heretofore used or described in the chemical literature.

Preferably the oxidation is carried out under mild, neutral conditions, for example, by reaction with (1) dimethyl sulphide-N-chlorosuccinimide complex, thioanisole-N-chlorosuccinimide complex, dimethyl sulphide-chlorine complex or thioanisole-chlorine complex in a haloalkane, e.g. chloroform, methylene chloride or carbon tetrachloride, or toluene at a temperature of from −30° C. to 0° C. [cf. J. Amer. Chem. Soc., 94, 7586 (1972)], (2) chromium trioxide-pyridine complex, e.g. Collins' reagent, in a haloalkane, e.g. chloroform, methylene chloride or carbon tetrachloride, at a temperature of from 0° C. to ambient, preferably at 0° C., or (3) Jones' reagent in the presence of acetone and dilute sulphuric acid at a temperature of from 0° C. to ambient.

Compounds of general formula VI, wherein Z represents ethylene and the other symbols are as hereinbefore defined, i.e. compounds of the general formula:

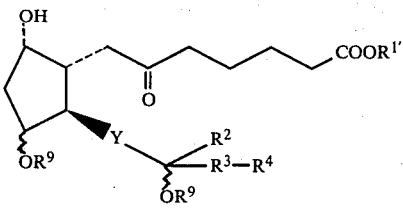

VIA (wherein the various symbols are as hereinbefore defined) may be prepared by hydrolysis under acidic conditions of a compound of the general formula:

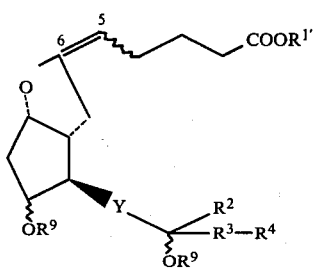

VII wherein the wavy line ⌇ attached to the carbon atom in position 5 indicates that the double bond between $C_5$–$C_6$ is Z or E and the other symbols are as hereinbefore defined.

The hydrolysis must be carried out carefully to avoid the elimination of the groups $R^9$, and may be carried out with an aqueous solution of an organic acid, e.g. acetic acid, propionic acid, oxalic acid or p-toluenesulphonic acid, or an aqueous solution of an inorganic acid, e.g. hydrochloric or sulphuric acid, in the presence or absence of an inert organic solvent miscible with water, e.g. an ether such as 1,2-dimethoxyethane, dioxan or tetrahydrofuran (preferably tetrahydrofuran), at a temperature of from 0° C. to 75° C. (preferably from 0° C. to ambient). Advantageously the hydrolysis may be carried out with a mixture of acetic acid, water and tetrahydrofuran, a mixture of dilute hydrochloric acid and tetrahydrofuran, or dilute hydrochloric acid. The progress of the hydrolysis is preferably monitored by thin layer chromatography to avoid elimination of the groups $R^9$.

Compounds of general formula VII are prepared by dehydrohalogenation of a compound of the general formula:

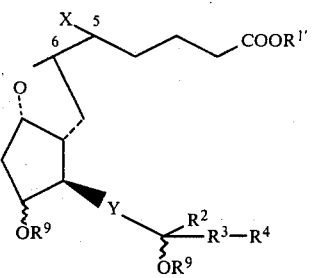

VIII wherein X represents a bromine or iodine atom, the absolute configurations of $C_5$ and $C_6$ are (5S, 6S), (5R, 6R), (5S, 6R) or (5R, 6S) or a mixture thereof, and the other symbols are as hereinbefore defined.

The dehydrohalogenation may be carried out with a known dehydrohalogenation reagent, for example (1) when X represents a bromine atom, a bicycloamine such as DBU (i.e. 1,5-diazabicyclo[5.4.0]undecene-5), DBN (i.e. 1,5-diazabicyclo[4.3.0]nonene-5) or DABCO (i.e. 1,4-diazabicyclo[2.2.2]octane), or an alkali metal, e.g. sodium or potassium, alcoholate containing from 1 to 4 carbon atoms, or (2) when X represents an iodine atom, a bicycloamine such as DBN, DBU or DABCO, or an alkali metal, e.g. sodium or potassium, alcoholate containing from 1 to 4 carbon atoms, superoxide, carbonate, hydroxide, benzoate, acetate, trifluoroacetate or bicarbonate, or silver acetate, or tetramethylammonium superoxide. The reaction may be carried out at a temperature from ambient to 110° C., preferably at a temperature from ambient to 80° C., and (1) when the reagent is a bicycloamine, optionally in the presence of an inert organic solvent, preferably in the absence of an inert organic solvent or in the presence of toluene or benzene, or (2) when the reagent is other than a bicycloamine, in the presence of an inert organic solvent, e.g. an alkanol containing from 1 to 4 carbon atoms, such as methanol or ethanol, or N,N-dimethylformamide.

Compounds of general formula VIII may be prepared from a compound of the general formula:

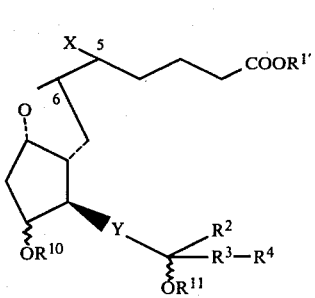

IX

[wherein $R^{10}$ and $R^{11}$, which may be the same or different, each represents a hydrogen atom, a tetrahydropyran-2-yl or tetrahydrofuran-2-yl group, each such group being unsubstituted or substituted by at least one alkyl group, or a 1-ethoxyethyl group, the absolute configurations of $C_5$ and $C_6$ are (5S, 6S), (5R, 6R), (5S, 6R) or (5R, 6S) or a mixture thereof and, the other symbols are as hereinbefore defined], when one or both of the symbols $R^{10}$ and $R^{11}$ represents hydrogen, by reaction of the compound of general formula IX with a 2,3-dihydropyran, 2,3-dihydrofuran or ethyl vinyl ether in an inert organic solvent, e.g. methylene chloride, in the presence of a condensing agent, e.g. p-toluenesulphonic acid. It will be appreciated that compounds of general formula VIII fall within the scope of general formula IX when R¹⁰ and R¹¹ both represent a tetrahydropyran-2-yl or tetrahydrofuran-2-yl group, each such group being unsubstituted or substituted by at least one alkyl group, or a 1-ethoxyethyl group.

Compounds of general formula IX, wherein the absolute configurations at $C_5$ and $C_6$ are (5R, 6R) or (5S, 6S) or a mixture thereof and the other symbols are as hereinbefore defined, may be prepared by bromination or iodination, and simultaneous cyclisation of a compound of the general formula:

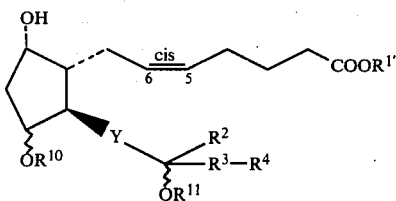

wherein the double bond between $C_5$–$C_6$ is cis and the various symbols are as hereinbefore defined.

The conversion of a compound of general formula X to a compound of general formula IX may be suitably carried out, (1) when X in the compound of general formula IX represents a bromine atom, with N-bromosuccinimide or N-bromoacetamide in an aprotic organic solvent, e.g. methylene chloride, chloroform, carbon tetrachloride, diethyl ether, N,N-dimethylformamide or tetrahydrofuran, or a mixture of two or more of them, at a temperature of from −30° to 70° C., or (2) when X in the compound of general formula IX represents an iodine atom, with (i) iodine in pyridine, (ii) potassium periodate and potassium iodide in aqueous acetic acid, (iii) iodine and potassium iodide in the presence of an alkali metal, e.g. sodium or potassium, carbonate or bicarbonate in water, or (iv) iodine in the presence of an alkali metal, e.g. sodium or potassium, carbonate in an inert organic solvent, e.g. methylene chloride or chloroform, at a temperature of from 0° C. to ambient. The product of general formula IX, thus obtained, is a mixture of isomers in which the absolute configurations of $C_5$ and $C_6$ are (5R, 6R) and (5S, 6S). If desired, the mixture may be separated by column, thin layer or high-speed liquid chromatography on silica gel to give each of the isomers, although such separation is not required.

Compounds of general formula IX, wherein the absolute configurations at $C_5$ and $C_6$ are (5R, 6S) or (5S, 6R) or a mixture thereof and the various symbols are as hereinbefore defined, may be prepared from a compound of the general formula:

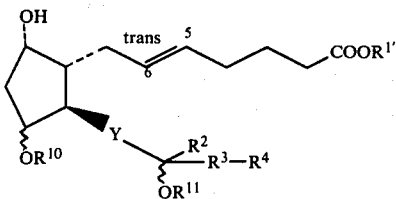

(wherein the double bond between $C_5$–$C_6$ is trans and the various symbols are as hereinbefore defined) by means heretofore mentioned for the conversion of compounds of general formula X to those of general formula IX. The product of general formula IX, thus obtained, is a mixture of isomers in which the absolute configurations of $C_5$ and $C_6$ are (5R, 6S) and (5S, 6R). If desired, the mixture may be separated by column, thin layer or high-speed liquid chromatography on silica gel to give each of the isomers, although such separation is not required.

Compounds of general formula XI may be prepared by photoisomerization of compounds of general formula X with light from a high pressure mercury lamp in the presence of diphenyl sulphide or diphenyl disulphide in an inert organic solvent, e.g. a mixture of benzene and methanol, at room temperature. The product obtained may be purified by column or thin layer chromatography on silica gel pretreated with silver nitrate to give compounds of general formula XI.

Compounds of general formula VI, wherein Z represents trans-vinylene and the other symbols are as hereinbefore defined, i.e. compounds of the general formula:

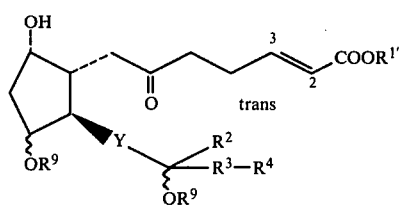

(wherein the double bond between $C_2$–$C_3$ is trans and the various symbols are as hereinbefore defined), may be prepared from a compound of the general formula:

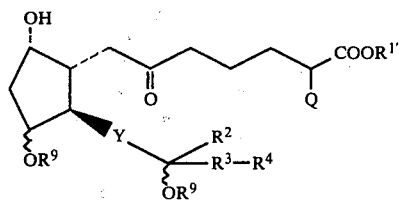

wherein Q represents the group —SeC₆H₅ or —SR¹², wherein R¹² represents an alkyl group containing from 1 to 4 carbon atoms or a phenyl group, and the other symbols are as hereinbefore defined.

Compounds of general formula XII, wherein Q represents the group —SeC₆H₅, may be converted to compounds of general formula VIB by reaction (1) with hydrogen peroxide in a mixture of ethyl acetate and tetrahydrofuran or methanol, preferably in the presence of sodium bicarbonate at a temperature below 30° C., or (2) with sodium periodate in a mixture of water and a lower alkanol, e.g. methanol or ethanol, preferably in the presence of sodium bicarbonate at a temperature below 30° C.

Compounds of general formula XII, wherein Q represents the group —SR¹², may be converted to compounds of the general formula:

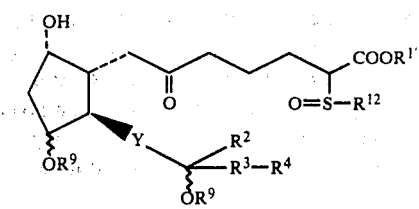

(wherein the various symbols are as hereinbefore defined) by means heretofore mentioned for the conversion of compounds of general formula XII, wherein Q represents the group —SeC$_6$H$_5$, to those of general formula VIB.

Compounds of general formula XIII may be converted to compounds of general formula VIB by treatment (1) when R$^{12}$ represents an alkyl group, in toluene, preferably in the presence of a small amount of calcium carbonate, at a temperature of 100° to 120° C. or (2) when R$^{12}$ represents a phenyl group, in carbon tetrachloride, preferably in the presence of a small amount of calcium carbonate, at a temperature of about 50° C.

Compounds of general formula XII may be prepared from a compound of the general formula:

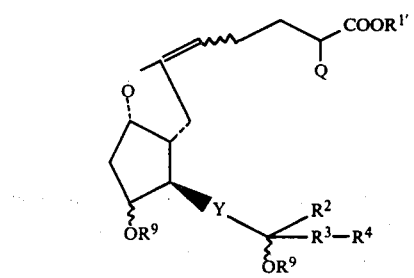

(wherein the wavy line attached to the carbon atom in position 5 indicates that the double bond between C$_5$-C$_6$ is Z or E and the other symbols are as hereinbefore defined) by means heretofore mentioned for the conversion of compounds of general formula VII to those of general formula VIA.

Compounds of general formula XIV may be prepared from a compound of the general formula:

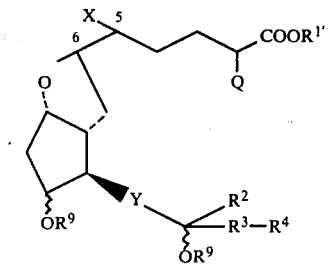

[wherein the absolute configurations of C$_5$ and C$_6$ are (5S, 6S), (5R, 6R), (5S, 6R) or (5R, 6S) or a mixture thereof and the various symbols are as hereinbefore defined] by means heretofore mentioned for the conversion of compounds of general formula VIII to those of general formula VII.

Compounds of general formula XV may be prepared from a compound of the general formula:

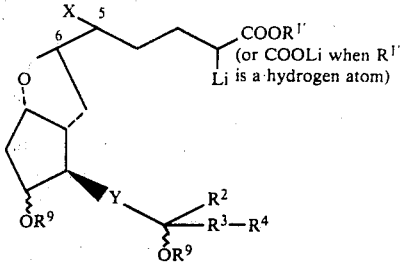

[wherein the absolute configurations of C$_5$ and C$_6$ are (5S, 6S), (5R, 6R), (5S, 6R) or (5R, 6S) or a mixture thereof and the other symbols are as hereinbefore defined] by reaction with benzeneselenenyl bromide (i.e. C$_6$H$_5$SeBr) or diphenyl diselenide (i.e. C$_6$H$_5$SeSeC$_6$H$_5$), or a dialkyl disulphide of the formula R$^{12}$SSR$^{12}$, wherein R$^{12}$ is as hereinbefore defined, in an inert organic solvent, e.g. tetrahydrofuran, hexamethylphosphotriamide, diethyl ether, n-hexane or p-pentane or a mixture of two or more of then, at a low temperature (when R$^{1\prime}$ is an alkyl group, at −78° C., or, when R$^{1\prime}$ is a hydrogen atom, at 0° C.) followed by hydrolysis of the resulting organolithium compound, for example by treatment with an aqueous solution of ammonium chloride to give compounds of general formula XV.

Compounds of general formula XVI may be prepared from a compound of general formula VIII by reaction with a compound of general formula:

(wherein R$^{13}$ and R$^{14}$ each represent an alkyl group containing from 1 to 6 carbon atoms or a cycloalkyl group containing from 3 to 6 carbon atoms), (1) when R$^{1\prime}$ represents an alkyl group, in tetrahydrofuran at a low temperature, e.g. at −78° C., or (2) when R$^{1\prime}$ represents a hydrogen atom, in tetrahydrofuran in the presence of hexamethylphosphotriamide at 0° C.

According to a further feature of the present invention, the prostaglandin E$_1$ analogues of general formula IV, wherein R$^1$ represents a hydrogen atom or a straight- or branched-chain alkyl group containing from 1 to 12 carbon atoms and the other symbols are as hereinbefore defined, may also be prepared by the hydrolysis to hydroxy groups of the groups —OR$^{15}$ and —OR$^{16}$ of a compound of the general formula:

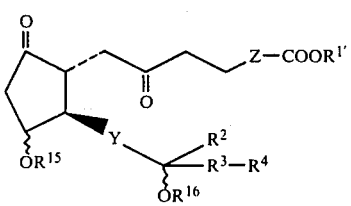

(wherein R$^{15}$ and R$^{16}$, which may be the same or different, each represent a tetrahydropyran-2-yl or tetrahydrofuran-2-yl group, each such group being unsubstituted or substituted by at least one alkyl group, a 1-ethoxyethyl group, or a trimethylsilyl group, with the proviso that at least one of the symbols $R^{15}$ and $R^{16}$ represents a trimethylsilyl group, and the other symbols are as hereinbefore defined) by means heretofore mentioned for the conversion of compounds of general formula V to those of general formula IV.

Compounds of general formula XVIII may be prepared from a compound of the general formula:

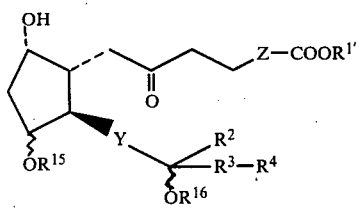
XIX (wherein the various symbols are as hereinbefore defined) by means heretofore mentioned for the conversion of compounds of general formula VI to those of general formula V.

Compounds of general formula XIX may be prepared from a compound of the general formula:

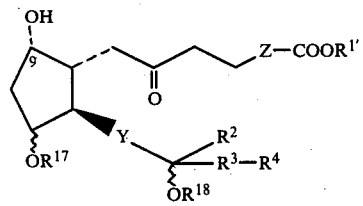
XX (wherein $R^{17}$ and $R^{18}$, which may be the same or different, each represent a hydrogen atom, a tetrahydropyran-2-yl or tetrahydrofuran-2-yl group, each such group being unsubstituted or substituted by at least one alkyl group, or a 1-ethoxyethyl group with the proviso that at least one of the symbols $R^{17}$ and $R^{18}$ represents a hydrogen atom, and the other symbols are as hereinbefore defined) by reaction with a suitable trimethylsilylating reagent, e.g. N-trimethylsilyldiethylamine or N,O-bis(-trimethylsilyl)acetamide, in an inert organic solvent, e.g. acetone or methylene chloride, preferably at room temperature.

Compounds of general formula XX, wherein Z represents ethylene and the other symbols are as hereinbefore defined, i.e. compounds of the general formula:

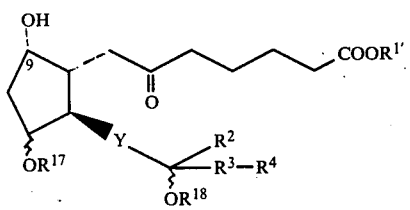
XXA (wherein the various symbols are as hereinbefore defined) may be prepared from a compound of general formula IX, wherein at least one of the symbols $R^{10}$ and $R^{11}$ represents a hydrogen atom, by means heretofore mentioned for the conversion of compounds of general formula VIII to those of general formula VIA via compounds of general formula VII.

Compounds of general formula XX, wherein Z represents trans-vinylene and the other symbols are as hereinbefore defined, i.e. compounds of the general formula:

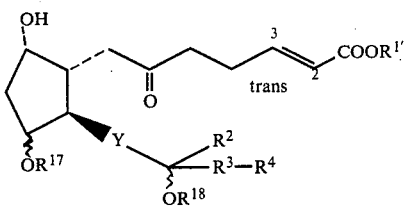
XXB (wherein the double bond between $C_2$-$C_3$ is trans and the various symbols are as hereinbefore defined) may be prepared from a compound of general formula IX, wherein at least one of the symbols $R^{10}$ and $R^{11}$ represents a hydrogen atom, by means heretofore mentioned for the conversion of compounds of general formula VIII to those of general formula VIB via compounds of general formula XVI, XV, XIV and XII.

If desired, the compounds of general formula IX or X, wherein $R^{1'}$ is other than a hydrogen atom and the other symbols are as hereinbefore defined, may be prepared by esterification of a compound of general formula IX or X, wherein $R^{1'}$ is a hydrogen atom and the other symbols are as hereinbefore defined, by methods known per se for the esterification of carboxylic acids, for example, by reaction with (i) the appropriate diazoalkane, e.g. diazomethane, in an inert organic solvent, e.g. diethyl ether, at a temperature of from $-10°$ to $25°$ C. and preferably $0°$ C., (ii) the appropriate alcohol in the presence of dicyclohexylcarbodiimide as condensing agent, or (iii) the appropriate alcohol following the formation of a mixed acid anhydride by adding a tertiary amine and then a pivaloyl halide or an arylsulphonyl or alkylsulphonyl halide (cf. our British Pat. Nos. 1,362,956 and 1,364,125).

If desired, the acids of general formula VI, VII, VIII, IX, XII, XIII, XIV or XV, wherein $R^{1'}$ represents a hydrogen atom, and the other symbols are as hereinbefore defined, may be prepared from the corresponding esters of general formula VI, VII, VIII, IX, XII, XIII, XIV or XV, wherein $R^{1'}$ is other than a hydrogen atom, and the other symbols are as hereinbefore defined, by alkaline hydrolysis with an aqueous solution of an alkali metal, e.g. sodium or potassium, hydroxide or carbonate in the presence of an inert organic solvent miscible with water, e.g. a lower alkanol such as methanol or ethanol, preferably at ambient temperature.

Starting materials of general formula X may be prepared by the methods described in the following patent specifications and applications, or obvious modifications thereof:

(1) when $R^2$ is a hydrogen atom or a methyl or ethyl group and the grouping $-R^3-R^4$ is a straight- or branched-chain alkyl group, as described in Japanese Patent Kokai Nos. 49-124048, 49-134656, 50-13362, 50-25549, 50-101340 and 51-68547, British Patent Specifications Nos. 1398291, 1450691, 1464916 and 1483240, and U.S. Pat. Nos. 3,962,312, 3,966,792 and 4,024,174;

(2) when $R^2$ is a hydrogen atom or a methyl or ethyl group, $R^3$ is a single bond or a straight- or branched-chain alkylene group and $R^4$ is an unsubstituted or substituted cycloalkyl group, as described in Japanese Patent Kokai Nos. 50-13364, 50-25549, 50-148339 and 51-68547, British Patent Specifications Nos. 1450691, 1464916, 1488141, 1483240 and 1484210, British Patent Applications Nos. 30072/75 and 18651/76, U.S. Pat. Nos. 3,962,312, 3,966,792, 4,034,003, 4,024,174, 4,045,468 and 4,087,620 and Belgian Patent No. 844256;

(3) when $R^2$ is a hydrogen atom or a methyl or ethyl group, $R^3$ is a single bond or a straight- or branched-chain alkylene group and $R^4$ is an unsubstituted or substituted phenyl group, as described in Japanese Patent Kokai Nos. 50-13364, 50-25549 and 51-68547, British Patent Specifications Nos. 1450691 and 1483240 and U.S. Pat. Nos. 3,962,312 and 4,024,174;

(4) when $R^2$ is a hydrogen atom or a methyl or ethyl group, $R^3$ is a single bond or a straight- or branched-chain alkylene group and $R^4$ is an unsubstituted or substituted phenoxy group, as described in Japanese Patent Kokai No. 51-59841 or 52-25745, British Patent Specification No. 1521747, U.S. Pat. No. 4,065,632 and Belgian Patent No. 845348.

(5) When $R^2$ is a hydrogen atom, $R^3$ is a single bond and $R^4$ is a hydrogen atom, from compounds of general formula XXI depicted hereafter, which may be prepared as described in British Patent Specification No. 1482928, by the series of reactions depicted schematically below in Scheme A, wherein $R^{19}$ represents an alkanoyl group containing from 2 to 5 carbon atoms and the other symbols are as hereinbefore defined.

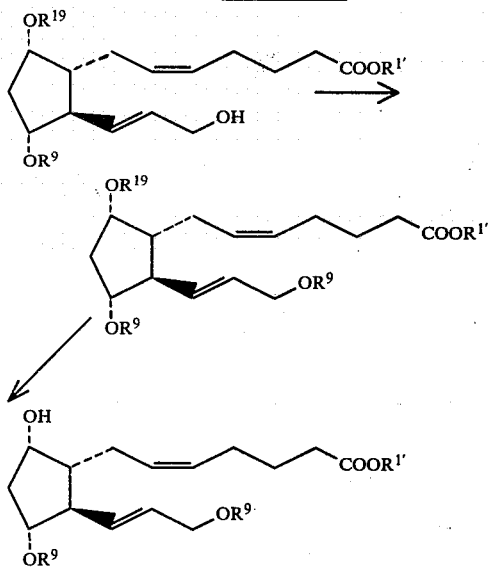

Compounds of the general formula XXI may be converted into compounds of general formula XXII by reaction with a dihydropyran, dihydrofuran or ethyl vinyl ether in an inert solvent, e.g. methylene chloride, in the presence of a condensing agent, e.g. p-toluenesulphonic acid.

Compounds of the general formula XXII may be converted into compounds of the general formula XA by hydrolysis under alkaline conditions, which may be effected with anhydrous potassium carbonate in an anhydrous alkanol containing at most four carbon atoms, preferably absolute methanol.

According to a further feature of the present invention esters of the prostaglandin $E_1$ analogues of general formula IV may be prepared by esterification of the corresponding acid of general formula IV wherein $R^1$ represents a hydrogen atom by methods known per se for example by reaction with (i) the appropriate diazoalkane in an inert organic solvent, e.g. diethyl ether, at a temperature of from $-10°$ to $25°$ C. and preferably $0°$ C., (ii) the appropriate alcohol in the presence of dicyclohexylcarbodiimide as condensing agent, or (iii) the appropriate alcohol following formation of a mixed anhydride by adding a tertiary amine and pivaloyl halide or an alkylsulphonyl or arylsulphonyl halide (cf. our British Pat. Nos. 1,362,956 and 1,364,125).

Prostaglandin analogues of general formula IV, wherein $R^1$ represents a group $-C_mH_{2m}COOR^5$, in which $R^5$ represents a hydrogen atom, may be esterified by methods known per se to obtain the corresponding esters in which $R^1$ represents a group $-C_mH_{2m}COOR^5$ in which $R^5$ represents a straight- or branched-chain alkyl group containing from 1 to 4 carbon atoms.

Cyclodextrin clathrates of the prostaglandin analogues of general formula IV may be prepared by dissolving the cyclodextrin in water or an organic solvent which is miscible with water and adding to the solution the prostaglandin analogue in a water-miscible organic solvent. The mixture is then heated and the desired cyclodextrin clathrate product isolated by concentrating the mixture under reduced pressure or by cooling and separating the product by filtration or decantation. The ratio of organic solvent to water may be varied according to the solubilities of the starting materials and products. Preferably the temperature is not allowed to exceed $70°$ C. during the preparation of the cyclodextrin clathrates. $\alpha$-, $\beta$- or $\gamma$-Cyclodextrins or mixtures thereof may be used in the preparation of the cyclodextrin clathrates. Conversion into their cyclodextrin clathrates serves to increase the stability of the prostaglandin analogues.

Compounds of general formula IV wherein $R^1$ represents a hydrogen atom or a group $-C_mH_{2m}COOR^5$ in which $R^5$ represents a hydrogen atom may, if desired, be converted by methods known per se into salts. Preferably the salts are non-toxic salts. By the term "non-toxic salts" as used in this specification, is meant salts the cations of which are relatively innocuous to the animal organism when used in therapeutic doses so that the beneficial pharmacological properties of the compounds of general formula IV are not vitiated by side-effects ascribable to those cations. Preferably the salts are water-soluble. Suitable non-toxic salts include the alkali metal, e.g. sodium or potassium, salts, the alkaline earth metal, e.g. calcium or magnesium, salts and ammonium salts, and pharmaceutically acceptable, (i.e. non-toxic) amine salts. Amines suitable for forming such salts with carboxylic acids are well known and include for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing from 1 to 3 carbon atoms. Suitable non-toxic amine salts are, e.g. tetraalkylammonium, such as tetramethylammonium, salts, and other organic amine salts such as methylamine salts, dimethylamine salts, cyclopentylamine salts, benzylamine salts, phenethylamine salts, piperidine salts monoethanolamine salts, diethanolamine salts, lysine salts or arginine salts.

Salts may be prepared from the acids of general formula IV wherein $R^1$ represents a hydrogen atom or a group $-C_mH_{2m}COOR^5$ in which $R^5$ represents a hydrogen atom, by methods known per se, for example by reaction of stoichiometric quantities of an acid of general formula IV and the appropriate base, e.g. an alkali metal or alkaline earth metal hydroxide or carbonate, ammonium hydroxide, ammonia or an organic amine in a suitable solvent. The salts may be isolated by lyophilisation of the solution or, if sufficiently insoluble in the reaction medium, by filtration, if necessary after removal of part of the solvent.

Prostaglandin analogues of general formula IV wherein $R^1$ represents a group

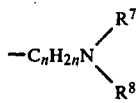

wherein n, $R^7$ and $R^8$ are as hereinbefore defined may be converted by methods known per se into acid addition salts, which are preferably non-toxic. Suitable acid addition salts are those formed with inorganic acids (such as hydrochlorides and sulphates) and with organic acids (such as acetates, propionates, succinates and benzoates).

The prostaglandin $E_1$ analogues of general formula IV and their cyclodextrin clathrates and, when $R^1$ represents a hydrogen atom or a group $-C_mH_{2m}COOR^5$ in which $R^5$ represents a hydrogen atom, and m is as hereinbefore defined, non-toxic salts and, when $R^1$ represents a group

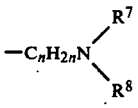

in which n, $R^7$ and $R^8$ are as hereinbefore defined, non-toxic acid addition salts, possess the valuable pharmacological properties typical of the prostaglandins in the selective fashion, in particular hypotensive activity, inhibitory activity on blood platelet aggregation, inhibitory activity on gastric acid secretion and gastric ulceration, stimulatory activity on uterine contraction and abortifacient, luteolytic and antinidatory activity, and are useful in the treatment of hypertension, in the treatment of disorders of the peripheral circulation, in the prevention and treatment of cerebral thrombosis and myocardial infarction, in the treatment of gastric ulceration, in the termination of pregnancy and induction of labour in pregnant female mammals, in the treatment of impaired fertility and in the control of oestrus, contraception and menstrual regulation in female mammals. For example, in standard laboratory tests, (i) by intravenous administration to the allobarbital-anaesthetized dog, 6-oxo-$PGE_1$ methyl ester produces a fall in blood pressure of 20 mm Hg and 44 mm Hg lasting 8 to 12 minutes at the doses of 0.5 and 1.0 μg/kg animal body weight, respectively, 6-oxo-16S-methyl-$PGE_1$ methyl ester produces a fall in blood pressure of 22 mm Hg and 36 mm Hg lasting 9 and 13 minutes at the doses of 0.05 and 0.1 μg/kg animal body weight, respectively, 6-oxo-17S-methyl-$PGE_1$ methyl ester produces a fall in blood pressure of 20 mm Hg and 60 mm Hg lasting 8 and 18 minutes at the doses of 0.5 and 1.0 μg/kg animal body weight, respectively, 6-oxo-trans-2,3-didehydro-$PGE_1$ methyl ester produces a fall in blood pressure of 22 mm Hg and 50 mm Hg lasting 22 and 53 minutes at the doses of 4 and 10 μg/kg animal body weight, respectively, 6-oxo-15-(3-propylcyclopentyl)-16,17,18,19,20-pentanor-$PGE_1$ methyl ester produces a fall in blood pressure of 34 mm Hg and 60 mm Hg lasting 8 and 20 minutes at the doses of 0.1 and 0.2 μg/kg animal body weight, respectively, 6-oxo-16-(3-chlorophenoxy)-17,18,19,20-tetranor-$PGE_1$ methyl ester produces a fall in blood pressure of 12 mm Hg and 40 mm Hg lasting 11 and 23 minutes at the doses of 2 and 10 μg/kg animal body weight, respectively, 6-oxo-15RS-methyl-$PGE_1$ methyl ester produces a fall in blood pressure of 10 mm Hg and 32 mm Hg lasting 9 and 17 minutes at the doses of 4 and 10 μg/kg animal body weight, respectively, 6-oxo-15-(3-propylcyclopentyl)-16,17,18,19,20-pentanor-$PGE_1$ produces a fall in blood pressure of 18 mm Hg and 34 mm Hg lasting 7 and 11 minutes at the doses of 0.05 and 0.1 μg/kg animal body weight, respectively, 6-oxo-15-(4-propylcyclohexyl)-16,17,18,19,20-pentanor-$PGE_1$ methyl ester produces a fall in blood pressure of 26 mm Hg and 42 mm Hg lasting 8 and 14 minutes at the doses of 0.2 and 0.5 μg/kg animal body weight, respectively, 6-oxo-17S,20-dimethyl-$PGE_1$ methyl ester produces a fall in bloood pressure of 32 mm Hg and 60 mm Hg lasting 8 and 11 minutes at the doses of 0.2 and 0.5 μg/kg animal body weight, respectively, 6-oxo-17S-methyl-20-ethyl-$PGE_1$ methyl ester produces a fall in blood pressure of 30 mm Hg and 54 mm Hg lasting 10 and 12 minutes at the doses of 1 and 2 μg/kg animal body weight, respectively, and 6-oxo-15-(3-butylcyclopentyl)-16,17,18,19,20-pentanor-$PGE_1$ methyl ester produces a fall in blood pressure of 30 mm Hg and 70 mm Hg lasting 10 and 22 minutes at the doses of 0.2 and 0.5 μg/kg animal body weight, respectively, (ii) in increase of coronary flows in isolated rabbit hearts, 6-oxo-16S-methyl-$PGE_1$ methyl ester, 6-oxo-17S-methyl-$PGE_1$ methyl ester, 6-oxo-trans-2,3-didehydro-$PGE_1$ methyl ester, 6-oxo-15-(3-propylcyclopentyl)-16,17,18,19,20-pentanor-$PGE_1$ methyl ester and 6-oxo-15-(3-propylcyclopentyl)-16,17,18,19,20-pentanor-$PGE_1$ are 1–2 times, 1.3 times, 1.0 times, 10 times and 4.2 times, respectively, as potent as $PGE_1$, (iii) 6-oxo-$PGE_1$ methyl ester, 6-oxo-16S-methyl-$PGE_1$ methyl ester, 6-oxo-17S-methyl-$PGE_1$ methyl ester, 6-oxo-trans-2,3-didehydro-$PGE_1$ methyl ester, 6-oxo-15-(3-propylcyclopentyl)-16,17,18,19,20-pentanor-$PGE_1$ methyl ester, 6-oxo-15-(3-propylcyclopentyl)-16,17,18,19,20-pentanor-$PGE_1$ and 6-oxo-17S,20-dimethyl-$PGE_1$ methyl ester produce a 50% inhibition of adenosine diphosphate-induced blood platelet aggregation in platelet-rich plasma of rats at the concentrations of $7.5 \times 10^{-2}$ μg/ml, $1.6 \times 10^{-2}$ μg/ml, $5.6 \times 10^{-3}$ μg/ml, $6.2 \times 10^{-2}$ μg/ml, $2.9 \times 10^{-3}$ μg/ml, $3.1 \times 10^{-3}$ μg/ml and $1.8 \times 10^{-3}$ μg/ml, respectively, in comparison with controls, (iv) 6-oxo-16S-methyl-$PGE_1$ methyl ester, 6-oxo-15-(3-propylcyclopentyl)-16,17,18,19,20-pentanor-$PGE_1$ methyl ester, 6-oxo-15-(3-propylcyclopentyl)-16,17,18,19,20-pentanor-$PGE_1$. 6-oxo-15-(4-propylcyclohexyl)-16,17,18,19,20-pentanor-$PGE_1$ methyl ester and 6-oxo-17S,20-dimethyl-$PGE_1$ methyl ester produce an increase in gastric acid pH from 2.0–2.5 to at least 4.0 in 50% of pentagastrin-treated rats when perfused into the stomach at the rates of $\leq 0.25$, $\leq 0.5$, 0.7–0.9, $> 0.5$ and 0.44 μg/animal/minute, respectively, (v) in stress ulceration of rats [produced according to the method of Takagi and Okabe—Jap. J. Pharmac., 18, 9–18(1968) by soaking rats in a water bath at 19° C. for 6 hours], 6-oxo-$PGE_1$ methyl ester produces 63.47% inhibition of stress ulceration by oral administration at the dose of 500 μg/kg animal body weight, 6-oxo-16S-methyl-PGE$_1$ methyl ester produces 59.54% and 86.37% inhibitions of stress ulceration by oral administration at the doses of 10 and 20 μg/kg animal body weight, respectively, 6-oxo-17S-methyl-PGE$_1$ methyl ester produces 68.94% and 86.48% inhibition of stress ulceration by oral administration at the doses of 100 and 200 μg/kg animal body weight, respectively, 6-oxo-trans-2,3-didehydro-PGE$_1$ methyl ester produces 82.16% inhibition of stress ulceration by oral administration at the dose of 500 μg/kg animal body weight, 6-oxo-15-(3-propylcyclopentyl)-16,17,18,19,20-pentanor-PGE$_1$ methyl ester produces 65.75% and 90.31% inhibition of stress ulceration by oral administration at the doses of 50 and 100 μg/kg animal body weight, respectively, 6-oxo-15-(3-propylcyclopentyl)-16,17,18,19,20-pentanor-PGE$_1$, produces 62.19% and 80.95% inhibition of stress ulceration by oral administration at the doses of 20 and 50 μg/kg animal body weight, respectively, 6-oxo-15-(4-propylcyclohexyl)-16,17,18,19,20-pentanor-PGE$_1$ methyl ester produces 44.37% and 63.05% inhibition of stress ulceration by oral administration at the doses of 50 and 200 μg/kg animal body weight, respectively, 6-oxo-17S,20-dimethyl-PGE$_1$ methyl ester produces 74.06% and 61.52% inhibition of stress ulceration by oral administration at the doses of 10 and 20 μg/kg animal body weight, respectively, 6-oxo-17S-methyl-20-ethyl-PGE$_1$ methyl ester produces 52.10% and 81.24% inhibition of stress ulceration by oral administration at the doses of 100 and 200 μg/kg animal body weight, respectively, and 6-oxo-15-(3-butylcyclopentyl)-16,17,18,19,20-pentanor-PGE$_1$ methyl ester produces 42.26% and 50.00% inhibition of stress ulceration by oral administration at the doses of 10 and 20 μg/kg animal body weight, respectively, (vi) in indomethacin-induced ulceration of rats, 6-oxo-16S-methyl-PGE$_1$ methyl ester produces 86.03% inhibition of indomethacin-induced ulceration by oral administration at the dose of 10 μg/kg animal body weight, 6-oxo-17S-methyl-PGE$_1$ methyl ester produces 70.13% inhibition of indomethacininduced ulceration by oral administration at the dose of 10 μg/kg animal body weight, 6-oxo-15-(3-propylcyclopentyl)-16,17,18,19,20-pentanor-PGE$_1$ methyl ester produces 89.9% inhibition of indomethacin-induced ulceration by oral administration at the dose of 5.0 μg/kg animal body weight, 6-oxo-15-(3-propylcyclopentyl)-16,17,18,19,20-pentanor-PGE$_1$ produces 86.87% inhibition of indomethacin-induced ulceration by oral administration at the dose of 10 μg/kg animal body weight, 6-oxo-17S,20-dimethyl-PGE$_1$ methyl ester produces 83.25% and 92.64% inhibitions of indomethacin-induced ulceration by oral administration at the doses of 5 and 10 μg/kg animal body weight, respectively, and 6-oxo-15-(3-butylcyclopentyl)-16,17,18,19,20-pentanor-PGE$_1$ methyl ester produces 66.83% and 63.40% inhibition of indomethacin-induced ulceration by oral administration at the doses of 2.5 and 5 μg/kg animal body weight, respectively, and (vii) 6-oxo-PGE$_1$ methyl ester, 6-oxo-16S-methyl-PGE$_1$ methyl ester, 6-oxo-17S-methyl-PGE$_1$ methyl ester, 6-oxo-trans-2,3-didehydro-PGE$_1$ methyl ester, 6-oxo-15-(3-propylcyclopentyl)-16,17,18,19,20-pentanor-PGE$_1$ methyl ester, 6-oxo-16-(3-chlorophenoxy)-17,18,19,20-tetranor-PGE$_1$ methyl ester and 6-oxo-15RS-methyl-PGE$_1$ methyl ester stimulate uterine contraction in the pregnant female rat when administered intravenously on the 20th day of gestation at the doses of 0.5, 0.1, 10-20, 2-5, 2-5, 0.5 and 1 μg/kg animal body weight, respectively.

The prostaglandin analogues of the present invention, their cyclodextrin clathrates, non-toxic salts and non-toxic acid addition salts can cause diarrhoea. The doses by oral administration of 6-oxo-16S-methyl-PGE$_1$ methyl ester, 6-oxo-17S-methyl-PGE$_1$ methyl ester, 6-oxo-trans-2,3-didehydro-PGE$_1$ methyl ester, 6-oxo-15-(3-propylcyclopentyl)-16,17,18,19,20-pentanor-PGE$_1$ methyl ester, 6-oxo-16-(3-chlorophenoxy)-17,18,19,20-tetranor-PGE$_1$ methyl ester, 6-oxo-15RS-methyl-PGE$_1$ methyl ester, 6-oxo-15-(3-propylcyclopentyl)-16,17,18,19,20-pentanor-PGE$_1$, 6-oxo-15-(4-propylcyclohexyl)-16,17,18,19,20-pentanor-PGE$_1$ methyl ester, 6-oxo-17S,20-dimethyl-PGE$_1$ methyl ester and 6-oxo-15-(3-butylcyclopentyl)-16,17,18,19,20-pentanor-PGE$_1$ methyl ester required to produce diarrhoea in 50% of mice so treated are 0.05-0.1, ca. 10, ≧10, 5.0-10, 10-20, 1.0-5.0, 5.0-10, >10, >10 and 10-20 mg/kg animal body weight, respectively.

Preferred prostaglandin analogues of the present invention are as follows: 6-oxo-PGE$_1$, 6-oxo-16-methyl-PGE$_1$, 6-oxo-17-methyl-PGE$_1$, 6-oxo-18-methyl-PGE$_1$, 6-oxo-19-methyl-PGE$_1$, 6-oxo-16,16-dimethyl-PGE$_1$, 6-oxo-16,17-dimethyl-PGE$_1$, 6-oxo-16,19-dimethyl-PGE$_1$, 6-oxo-16-ethyl-PGE$_1$, 6-oxo-17-ethyl-PGE$_1$, 6-oxo-16-propyl-PGE$_1$, 6-oxo-17-propyl-PGE$_1$, 6-oxo-20-methyl-PGE$_1$, 6-oxo-16,20-dimethyl-PGE$_1$, 6-oxo-17,20-dimethyl-PGE$_1$, 6-oxo-16,16,20-trimethyl-PGE$_1$, 6-oxo-16-ethyl-20-methyl-PGE$_1$, 6-oxo-17-ethyl-20-methyl-PGE$_1$, 6-oxo-20-ethyl-PGE$_1$, 6-oxo-17-methyl-20-ethyl-PGE$_1$, 6-oxo-17,20-diethyl-PGE$_1$, 6-oxo-20-butyl-PGE$_1$, 6-oxo-20-hexyl-PGE$_1$, 6-oxo-15-cyclobutyl-16,17,18,19,20-pentanor-PGE$_1$, 6-oxo-15-(1-propylcyclobutyl)-16,17,18,19,20-pentanor-PGE$_1$, 6-oxo-15-(1-butylcyclobutyl)-16,17,18,19,20-pentanor-PGE$_1$, 6-oxo-15-(1-pentylcyclobutyl)-16,17,18,19,20-pentanor-PGE$_1$, 6-oxo-15-(1-hexylcyclobutyl)-16,17,18,19,20-pentanor-PGE$_1$, 6-oxo-15-(2-methylcyclobutyl)-16,17,18,19,20-pentanor-PGE$_1$, 6-oxo-15-(2-propylcyclobutyl)-16,17,18,19,20-pentanor-PGE$_1$, 6-oxo-15-(3-ethylcyclobutyl)-16,17,18,19,20-pentanor-PGE$_1$, 6-oxo-15-(3-propylcyclobutyl)-16,17,18,19,20-pentanor-PGE$_1$, 6-oxo-15-(2,3,4-triethylcyclobutyl)-16,17,18,19,20-pentanor-PGE$_1$, 6-oxo-15-cyclopentyl-16,17,18,19,20-pentanor-PGE$_1$, 6-oxo-16-cyclopentyl-17,18,19,20-tetranor-PGE$_1$, 6-oxo-17-cyclopentyl-18,19,20-trinor-PGE$_1$, 6-oxo-16-cyclopentyl-18,19,20-trinor-PGE$_1$, 6-oxo-18-cyclopentyl-19,20-dinor-PGE$_1$, 6-oxo-17-cyclopentyl-19,20-dinor-PGE$_1$, 6-oxo-15-(2-pentylcyclopentyl)-16,17,18,19,20-pentanor-PGE$_1$, 6-oxo-15-(2,2-dimethylcyclopentyl)-16,17,18,19,20-pentanor-PGE$_1$, 6-oxo-15-(3-ethylcyclopentyl)-16,17,18,19,20-pentanor-PGE$_1$, 6-oxo-15-(3-propylcyclopentyl)-16,17,18,19,20-pentanor-PGE$_1$, 6-oxo-15-(3-butylcyclopentyl)-16,17,18,19,20-pentanor-PGE$_1$, 6-oxo-15-(3-tert-butylcyclopentyl)-16,17,18,19,20-pentanor-PGE$_1$, 6-oxo-15-(1-methyl-3-propylcyclopentyl)-16,17,18,19,20-pentanor-PGE$_1$, 6-oxo-15-(2-methyl-3-propylcyclopentyl)-16,17,18,19,20-pentanor-PGE$_1$, 6-oxo-15-(2-methyl-4-propylcyclopentyl)-16,17,18,19,20-pentanor-PGE$_1$, 6-oxo-15-cyclohexyl-16,17,18,19,20-pentanor-PGE$_1$, 6-oxo-16-cyclohexyl-17,18,19,20-tetranor-PGE$_1$, 6-oxo-17-cyclohexyl-18,19,20-trinor-PGE$_1$, 6-oxo-16-cyclohexyl-18,19,20-trinor-PGE$_1$, 6-oxo-18-cyclohexyl-19,20-dinor-PGE$_1$, 6-oxo-16-methyl-17-cyclohexyl-18,19,20-trinor-PGE$_1$, 6-oxo-17-cyclohexyl-19,20-dinor-PGE$_1$, 6-oxo-16-methyl-16- cyclohexyl-18,19,20-trinor-PGE$_1$, 6-oxo-19-cyclohexyl-20-nor-PGE$_1$, 6-oxo-15-(3-ethylcyclohexyl)-16,17,18,19,20-pentanor-PGE$_1$, 6-oxo-15-(3-isopropylcyclohexyl)-16,17,18,19,20-pentanor-PGE$_1$, 6-oxo-15-(4-methylcyclohexyl)-16,17,18,19,20-pentanor-PGE$_1$, 6-oxo-15-(4-ethylcyclohexyl)-16,17,18,19,20-pentanor-PGE$_1$, 6-oxo-15-(4-propylcyclohexyl)-16,17,18,19,20-pentanor-PGE$_1$, 6-oxo-15-(4-butylcyclohexyl)-16,17,18,19,20-pentanor-PGE$_1$, 6-oxo-15-(4-tert-butylcyclohexyl)-16,17,18,19,20-pentanor-PGE$_1$, 6-oxo-15-(2,6-dimethylcyclohexyl)-16,17,18,19,20-pentanor-PGE$_1$, 6-oxo-15-(2,2-dimethylcyclohexyl)-16,17,18,19,20-pentanor-PGE$_1$, 6-oxo-15-(2,4,6-trimethylcyclohexyl)-16,17,18,19,20-pentanor-PGE$_1$, 6-oxo-16-(1-methylcyclohexyl)-17,18,19,20-tetranor-PGE$_1$, 6-oxo-15-cycloheptyl-16,17,18,19,20-pentanor-PGE$_1$, 6-oxo-16-cycloheptyl-17,18,19,20-tetranor-PGE$_1$, 6-oxo-17-cycloheptyl-18,19,20-trinor-PGE$_1$, 6-oxo-16-cycloheptyl-18,19,20-trinor-PGE$_1$, 6-oxo-15-phenyl-16,17,18,19,20-pentanor-PGE$_1$, 6-oxo-16-phenyl-17,18,19,20-tetranor-PGE$_1$, 6-oxo-16-phenyl-18,19,20-trinor-PGE$_1$, 6-oxo-17-phenyl-18,19,20-trinor-PGE$_1$, 6-oxo-16-phenoxy-17,18,19,20-tetranor-PGE$_1$, 6-oxo-16-(3-chlorophenoxy)-17,18,19,20-tetranor-PGE$_1$, 6-oxo-16-(4-chlorophenoxy)-17,18,19,20-tetranor-PGE$_1$, 6-oxo-16-(3-trifluoromethylphenoxy)-17,18,19,20-tetranor-PGE$_1$, and the corresponding 15-methyl- and 15-ethyl-PGE$_1$ analogues and their esters and non-toxic salts, and cyclodextrin clathrates of the PGE$_1$ and 15-methyl- and 15-ethyl-PGE$_1$ analogues and their esters.

Particularly preferred prostaglandin analogues of the invention are 6-oxo-PGE$_1$ methyl ester, 6-oxo-16S-methyl-PGE$_1$ methyl ester, 6-oxo-17S-methyl-PGE$_1$ methyl ester, 6-oxo-16-(3-chlorophenoxy)-17,18,19,20-tetranor-PGE$_1$ methyl ester, 6-oxo-15RS-methyl-PGE$_1$ methyl ester, 6-oxo-17S,20-dimethyl-PGE$_1$ methyl ester, 6-oxo-17S-methyl-20-ethyl-PGE$_1$ methyl ester and 6-oxo-trans-2,3-didehydro-PGE$_1$ methyl ester.

6-Oxo-15-(3-butylcyclopentyl)-16,17,18,19,20-pentanor-PGE$_1$ methyl ester, 6-oxo-15-(4-propylcyclohexyl)-16,17,18,19,20-pentanor-PGE$_1$ methyl ester, 6-oxo-15-(3-propylcyclopentyl)-16,17,18,19,20-pentanor PGE$_1$ methyl ester and 6-oxo-15-(3-propylcyclopentyl)-16,17,18,19,20-pentanor-PGE$_1$, are the most preferred prostaglandin analogues of the invention.

Compounds of formulae V, VI, XVIII and XIX are new and as such constitute a feature of the present invention.

The following Reference Examples and Examples illustrate the preparation of new prostaglandin E$_1$ analogues of the present invention. In them 'TLC', 'IR' and 'NMR' represent respectively 'Thin layer chromatography', 'Infrared absorption spectrum' and 'Nuclear magnetic resonance spectrum'. When solvent ratios are specified in chromatographic separations, the ratios are by volume.

REFERENCE EXAMPLE 1

(13E)-(5RS,6RS,9α,11α,15S)-5-Bromo-6,9-epoxy-11,15-bis(tetrahydropyran-2-yloxy)prost-13-enoic acid methyl ester Under an atmosphere of nitrogen, a solution of 3.4 g of (5Z,13E)-(9α,11α,15S)-9-hydroxy-11,15-bis(tetrahydropyran-2-yloxy)prosta-5,13-dienoic acid methyl ester in a mixture of 30 ml of methylene chloride and 6 ml of N,N-dimethylformamide was added dropwise to a suspension of 1.35 g of N-bromosuccinimide in 50 ml of methylene chloride at −20° to −10° C. and the mixture was stirred for 30 minutes at the same temperature. The reaction mixture was then poured into ice-water and extracted with diethyl ether. The extract was washed with water and an aqueous solution of sodium chloride, dried over magnesium sulphate and concentrated under reduced pressure. The residue was purified by column chromatography on silica gel using a mixture of cyclohexane and ethyl acetate (4:1) as eluent to give 3.43 g of the title compound having the following physical characteristics:

TLC (developing solvent, benzene:ethyl acetate=2:1).

Rf=0.65 and 0.69.

IR (liquid film): $\nu = 1745, 1440, 1030, 980$ cm$^{-1}$.

NMR (CDCl$_3$ solution): δ=5.72–5.30 (2H, m), 4.80–4.46 (3H, m), 4.32–2.32 (11H, m), 1.00–0.75 (3H, m).

The following compounds were prepared by the same procedure as described above.

(a) (13E)-(5RS,6RS,9α,11α,15S,16S)-5-Bromo-6,9-epoxy-11,15-bis(tetrahydropyran-2-yloxy)-16-methylprost-13-enoic acid methyl ester, having the following physical characteristics, was prepared from (5Z,13E)-(9α,11α,15S,16S)-9-hydroxy-11,15-bis(tetrahydropyran-2-yloxy)-16-methylprosta-5,13-dienoic acid methyl ester.

TLC (developing solvent, benzene:ethyl acetate:methanol; 19:38:1).

Rf=0.45 and 0.54.

IR (liquid film): $\nu = 1710, 1440, 1020, 980$ cm$^{-1}$.

NMR (CDCl$_3$ solution): δ=8.70 (1F, broad s), 5.70–5.25 (2H, m), 4.80–4.45 (3H, m), 4.23–3.25 (8H, m), 1.02–0.75 (6H, m).

(b) (13E)-(5RS,6RS,9α,11α,15S,17S)-5-Bromo-6,9-epoxy-11,15-bis(tetrahydropyran-2-yloxy)-17-methylprost-13-enoic acid methyl ester, having the following physical characteristics, was prepared from (5Z,13E)-(9α,11α,15S,17S)-9-hydroxy-11,15-bis(tetrahydropyran-2-yloxy)-17-methylprosta-5,13-dienoic acid methyl ester.

TLC (developing solvent, cyclohexane:ethyl acetate=4:1).

Rf=0.31.

IR (liquid film): $\nu = 2945, 2870, 1735, 1434$ cm$^{-1}$.

NMR (CDCl$_3$ solution): δ=5.75–5.28 (2H, m), 4.74–4.54 (2H, m), 3.67 (3H, s), 1.0–0.77 (6H, m).

REFERENCE EXAMPLE 2

(13E)-(5RS,6RS,9α,11α,15S)-5-Iodo-6,9-epoxy-11,15-bis(tetrahydropyran-2-yloxy)-15-(3-propylcyclopentyl)-16,17,18,19,20-pentanorprost-13-enoic acid methyl ester To a solution of 980 mg of (5Z,13E)-(9α,11α,15S)-9-hydroxy-11,15-bis(tetrahydropyran-2-yloxy)-15-(3-propylcyclopentyl)-16,17,18,19,20-pentanorprosta-5,13-dienoic acid methyl ester in 5 ml of methylene chloride was added a solution of 1.428 g of sodium bicarbonate in 15 ml of water and the mixture was cooled to 0° to 5° C. in an ice-bath. A solution of 0.475 g of iodine in 20 ml of methylene chloride at the same temperature was added in portions to the mixture and then the reaction mixture was stirred for 1 hour. An aqueous solution of sodium thiosulphate was added to the reaction mixture until the colour of iodine vanished. The reaction mixture was extracted with chloroform and the extract was dried over sodium sulphate and concentrated under reduced pressure. The residue was purified by column chromatography on silica gel using a mixture of cyclohexane and ethyl acetate (1:1) as eluent to give 974 mg of the title compound having the following physical characteristics:

TLC (developing solvent, cyclohexane:ethyl acetate=2:1).
Rf=0.60.
IR (liquid film): $\nu$=2950, 2875, 1742 cm$^{-1}$.
NMR (CDCl$_3$ solution): $\delta$=5.68–5.30 (2H, m), 4.78–4.48 (3H, m), 3.67 (3H, s), 0.98–0.76 (3H, m).

The following compounds were prepared by the same procedure as described above.

(a) (13E)-(5RS,6RS,9α,11α,15R)-5-Iodo-6,9-epoxy-11,15-bis(tetrahydropyran-2-yloxy)-16-(3-chlorophenoxy)-17,18,19,20-tetranorprost-13-enoic acid methyl ester, having the following physical characteristics, was prepared from (5Z,13E)-(9α,11α,15R)-9-hydroxy-11,15-bis(tetrahydropyran-2-yloxy)-16-(3-chlorophenoxy)-17,18,19,20-tetranorprosta-5,13-dienoic acid methyl ester.

TLC (developing solvent, cyclohexane:ethyl acetate=2:1).
Rf=0.57.
IR (liquid film): $\nu$=2935, 2850, 1740, 1590, 1580 cm$^{-1}$.
NMR (CDCl$_3$ solution): $\delta$=7.32–6.70 (4H, m), 5.90–5.50 (2H, m), 5.00–4.37 (4H, m), 3.68 (3H, s).

(b) (13E)-(5RS,6RS,9α,11α,15S)-5-Iodo-6,9-epoxy-11,15-bis(tetrahydropyran-2-yloxy)-15-(3-butylcyclopentyl)-16,17,18,19,20-pentanorprost-13-enoic acid methyl ester, having the following physical characteristic, was prepared from (5Z,13E)-(9α,11α,15S)-9-hydroxy-11,15-bis(tetrahydropyran-2-yloxy)-15-(3-butylcyclopentyl)-16,17,18,19,20-pentanorprosta-5,13-dienoic acid methyl ester.

TLC (developing solvent, cyclohexane:ethyl acetate=3:1).
Rf=0.67.

(c) (13E)-(5RS,6RS,9α,11α,15RS)-5-Iodo-6,9-epoxy-11,15-dihydroxy-15-methylprost-13-enoic acid methyl ester, having the following physical characteristics, was prepared from (5Z,13E)-(9α,11α,15RS)-9,11,15-trihydroxy-15-methylprosta-5,13-dienoic acid methyl ester.

TLC (developing solvent, ethyl acetate).
Rf=0.45.
IR (liquid film): $\nu$=2970, 2950, 2880, 1745 cm$^{-1}$.
NMR (CDCl$_3$ solution): $\delta$=5.82–5.3 (2H, m), 4.71–4.45 (1H, m), 4.3–3.7 (2H, m), 3.69 (3H, s).

(d) (13E)-(5RS,6RS,9α,11α,15S,17S)-5-Iodo-6,9-epoxy-11,15-dihydroxy-17,20-dimethylprost-13-enoic acid methyl ester, having the following physical characteristics, was prepared from (5Z,13E)-(9α,11α,15S,17S)-9,11,15-trihydroxy-17,20-dimethylprosta-5,13-dienoic acid methyl ester.

TLC (developing solvent, ethyl acetate).
Rf=0.42.
IR (liquid film): $\nu$=2980, 2950, 1850, 1750 cm$^{-1}$.
NMR (CDCl$_3$ solution): $\delta$=5.5–5.3 (2H, m), 3.54 (3H, s).

(e) (13E)-(5RS,6RS,9α,11α,15S,17S)-5-Iodo-6,9-epoxy-11-(tetrahydropyran-2-yloxy)-15-hydroxy-17-methyl-20-ethylprost-13-enoic acid methyl ester, having the following physical characteristics, was prepared from (5Z,13E)-(9α,11α,15S,17S)-9,15-dihydroxy-11-(tetrahydropyran-2-yloxy)-17-methyl-20-ethylprosta-5,13-dienoic acid methyl ester.

TLC (developing solvent, cyclohexane:ethyl acetate=1:1).
Rf=0.44.
IR (liquid film): $\nu$=2980, 2950, 2880, 1745 cm$^{-1}$.
NMR (CDCl$_3$ solution): $\delta$=5.45–5.36 (2H, m), 4.66–4.4 (1H, m), 3.57 (3H, s).

(f) (13E)-(5RS,6RS,9α,11α,15S)-5-Iodo-6,9-epoxy-11-(tetrahydropyran-2-yloxy)-15-hydroxy-15-(4-propylcyclohexyl)-16,17,18,19,20-pentanorprost-13-enoic acid methyl ester, having the following physical characteristic, was prepared from (5Z,13E)-(9α,11α,15S)-9,15-dihydroxy-11-(tetrahydropyran-2-yloxy)-15-(4-propylcyclohexyl)-16,17,18,19,20-pentanorprosta-5,13-dienoic acid methyl ester.

TLC (developing solvent, ethyl acetate:benzene=2:1).
Rf=0.60.

REFERENCE EXAMPLE 3

(13E)-(5RS,6RS,9α,11α,15RS)-5-Iodo-6,9-epoxy-11,15-bis(tetrahydropyran-2-yloxy)-15-methylprost-13-enoic acid methyl ester To a solution of 1.067 g of (13E)-(5RS,6RS,9α,11α,15RS)-5-iodo-6,9-epoxy-11,15-dihydroxy-15-methylprost-13-enoic acid methyl ester [prepared as described in Reference Example 2(c)] in 20 ml of methylene chloride were added 1.4 mg of p-toluenesulphonic acid and 1.337 g of 2,3-dihydropyran and the mixture was stirred at −4° C. for 4.5 hours. The reaction mixture was then neutralised with an aqueous solution of sodium bicarbonate and extracted with chloroform. The extract was dried over magnesium sulphate and concentrated under reduced pressure. The residue was purified by column chromatography on silica gel using a mixture of cyclohexane and ethyl acetate (2:1) as eluent to give 1.2 g of the title compound having the following physical characteristics:

TLC (developing solvent, cyclohexane:ethyl acetate=1:1).
Rf=0.67.
IR (liquid film): $\nu$=2950, 2880, 1745 cm$^{-1}$.
NMR (CDCl$_3$ solution): $\delta$=5.8–5.2 (2H, m) 5.1–4.3 (3H, m), 3.67 (3H, s).

The following compounds were prepared by the same procedure as described above.

(a) (13E)-(5RS,6RS,9α,11α,15S,17S)-5-Iodo-6,9-epoxy-11,15-bis(tetrahydropyran-2-yloxy)-17,20-dimethylprost-13-enoic acid methyl ester, having the following physical characteristics, was prepared from (13E)-(5RS,6RS,9α,11α,15S,17S)-5-iodo-6,9-epoxy-11,15-dihydroxy-17,20-dimethylprost-13-enoic acid methyl ester [prepared as described in Reference Example 2(d)].

TLC (developing solvent, ethyl acetate).
Rf=0.70.
IR (liquid film): $\nu$=2950, 2880, 1745 cm$^{-1}$.
NMR (CDCl$_3$ solution): $\delta$=5.5–5.12 (2H, m), 4.63–4.4 (2H, m), 3.54 (3H, s).

(b) (13E)-(5RS,6RS,9α,11α,15S,17S)-5-Iodo-6,9-epoxy-11,15-bis(tetrahydropyran-2-yloxy)-17-methyl-20-ethylprost-13-enoic acid methyl ester, having the following physical characteristics, was prepared from (13E)-(5RS,6RS,9α,11α,15S,17S)-5-iodo-6,9-epoxy-11-(tetrahydropyran-2-yloxy)-15-hydroxy-17-methyl-20-ethylprost-13-enoic acid methyl ester [prepared as described in Reference Example 2(e)].

TLC (developing solvent, cyclohexane:ethyl acetate=1:1).
Rf=0.58.

IR (liquid film): ν=2950, 2880, 1740 cm⁻¹.

(c) (13E)-(5RS,6RS,9α,11α,15S)-5-Iodo-6,9-epoxy-11,15-bis(tetrahydropyran-2-yloxy)-15-(4-propylcyclohexyl)-16,17,18,19,20-pentanorprost-13-enoic acid methyl ester, having the following physical characteristics, was prepared from (13E)-(5RS,6RS,9α,11α,15S)-5-iodo-6,9-epoxy-11-(tetrahydropyran-2-yloxy)-15-hydroxy-15-(4-propylcyclohexyl)-16,17,18,19,20-pentanorprost-13-enoic acid methyl ester [prepared as described in Reference Example 2(f)].

IR (liquid film): ν=2950, 2880, 1745 cm⁻¹.
NMR (CDCl₃ solution): δ=5.42–5.15 (2H, m), 4.6–4.3 (2H, m), 3.54 (3H, s).

REFERENCE EXAMPLE 4

(13E)-(5RS,6RS,9α,11α,15S)-2-Phenylseleno-5-bromo-6,9-epoxy-11,15-bis(tetrahydropyran-2-yloxy)prost-13-enoic acid methyl ester Under an atmosphere of nitrogen, 5.4 ml of a 1.5 M solution of n-butyllithium in n-hexane was added dropwise to a solution of 1.23 ml of diisopropylamine in 50 ml of tetrahydrofuran at −70° C. and the mixture was stirred at the same temperature for 15 minutes to give a solution of lithium diisopropylamide. To the solution obtained was added dropwise a solution of 4.149 g of (13E)-(5RS,6RS,9α,11α,15S)-5-bromo-6,9-epoxy-11,15-bis(tetrahydropyran-2-yloxy)prost-13-enoic acid methyl ester (prepared as described in Reference Example 1) in 1.5 ml of tetrahydrofuran at −70° C. and the mixture was stirred at the same temperature for 15 minutes. To the solution thus obtained was added dropwise a solution of 2.746 g of diphenyl diselenide in 15 ml of tetrahydrofuran at −70° C. and the mixture was stirred at the same temperature for 1.5 hours. The reaction mixture was then poured into a saturated aqueous solution of ammonium chloride and extracted with ethyl acetate. The extract was washed with water, 1 N hydrochloric acid, an aqueous solution of sodium bicarbonate and an aqueous solution of sodium chloride, dried over magnesium sulphate and concentrated under reduced pressure. The residue was purified by column chromatography on silica gel using a mixture of cyclohexane and ethyl acetate (5:1) as eluent to give 3.482 g of the title compound having the following physical characteristics:

TLC (developing solvent, cyclohexane:ethyl acetate=3:1).
Rf=0.29.
IR (liquid film): ν=1740, 1580, 1440, 980 cm⁻¹.

REFERENCE EXAMPLE 5

(5Z,13E)-(9α,11α,15S)-6,9-Epoxy-11,15-bis(tetrahydropyran-2-yloxy)-15-(3-propylcyclopentyl)-16,17,18,19,20-pentanorprosta-5,13-dienoic acid methyl ester Under an atmosphere of nitrogen, a solution of 929 mg of (13E)-(5RS,6RS,9α,11α,15S)-5-iodo-6,9-epoxy-11,15-bis(tetrahydropyran-2-yloxy)-15-(3-propylcyclopentyl)-16,17,18,19,20-pentanorprost-13-enoic acid methyl ester (prepared as described in Reference Example 2) and 3.2 ml of DBU (1,5-diazabicyclo[5.4.0]undec-ene-5) was stirred at 45° to 50° C. for 1.5 hours, and then cooled to 0° to 5° C. To the reaction mixture were added 11 ml of 1 N hydrochloric acid and 11 ml of phosphate buffer solution (pH 6.86) with cooling to 0° to 5° C. The reaction mixture was extracted quickly with diethyl ether. The extract was dried over magnesium sulphate and concentrated under reduced pressure at a temperature below 0° C. to give 743 mg of the title compound having the following physical characteristic:

IR (liquid film): ν=2960, 2880, 1740, 1695 cm⁻¹.

REFERENCE EXAMPLE 6

(5Z,13E)-(9α,11α,15S)-6,9-Epoxy-11,15-bis(tetrahydropyran-2-yloxy)-15-(3-propylcyclopentyl)-16,17,18,19,20-pentanorprosta-5,13-dienoic acid To a solution of 407.5 mg of (5Z,13E)-(9α,11α,15S)-6,9-epoxy-11,15-bis(tetrahydropyran-2-yloxy)-15-(3-propylcyclopentyl)-16,17,18,19,20-pentanorprosta-5,13-dienoic acid methyl ester (prepared as described in Reference Example 5) in 5 ml of methanol was added dropwise a solution of 160 mg of potassium hydroxide in 6.5 ml of water at room temperature, and the mixture was stirred for 24 hours at the same temperature to give the title compound. The reaction mixture thus obtained was used immediately in the next reaction [in Reference Example 9(a) described hereinafter].

REFERENCE EXAMPLE 7

(13E)-(9α,11α,15S)-6-Oxo-9-hydroxy-11,15-bis(tetrahydropyran-2-yloxy)prost-13-enoic acid methyl ester Under an atmosphere of nitrogen, a solution of 970 mg of (13E)-(5RS,6RS,9α,11α,15S)-5-bromo-6,9-epoxy-11,15-bis(tetrahydropyran-2-yloxy)prost-13-enoic acid methyl ester (prepared as described in Reference Example 1) and 2 ml of DBU was stirred at room temperature overnight, and then cooled to 0° C. 6 ml of water was added to the reaction mixture, which was then acidified to pH 1 with 1 N hydrochloric acid at 0° C., and extracted with ethyl acetate. The extract was washed with an aqueous solution of sodium bicarbonate and an aqueous solution of sodium chloride, dried over magnesium sulphate and concentrated under reduced pressure to give the crude title compound having the following physical characteristic:

TLC (developing solvent, ethyl acetate:n-hexane=1:1).
Rf=0.31.

REFERENCE EXAMPLE 8

(13E)-(9α,11α,15S,16S)-6-Oxo-9-hydroxy-11,15-bis(tetrahydropyran-2-yloxy)-16-methylprost-13-enoic acid methyl ester Under an atmosphere of nitrogen, a solution of 2.233 g of (13E)-(5RS,6RS,9α,11α,15S,16S)-5-bromo-6,9-epoxy-11,15-bis(tetrahydropyran-2-yloxy)-16-methylprost-13-enoic acid methyl ester [prepared as described in Reference Example 1(a)] and 7.4 ml of DBU was stirred at 70° C. for 3 hours, and then cooled to 0° C. To the reaction mixture were added 37 ml of 1 N hydrochloric acid and 37 ml of phosphate buffer solution (pH 6.68) with cooling to 0° C. The reaction mixture was extracted quickly with diethyl ether. The extract was dried over magnesium sulphate and concentrated under reduced pressure to give an oily product. To a solution of the oily product thus obtained in 40 ml of tetrahydrofuran were added dropwise 4 ml of water and 4 ml of 65% (v/v) aqueous acetic acid and the mixture was stirred at room temperature for 2 hours and then extracted with ethyl acetate. The extract was washed with water, an aqueous solution of sodium bicarbonate and an aqueous solution of sodium chloride, dried over magnesium sulphate and concentrated under reduced pressure. The residue was purified by column chromatography on silica gel using a mixture of cyclohexane and ethyl acetate (1:1) as eluent to give 1.323 g of the title compound having the following physical characteristics:

TLC (developing solvent, cyclohexane:ethyl acetate=1:1).

Rf=0.34.

IR (liquid film): $\nu$=3425, 1740, 1710, 970 cm$^{-1}$.

NMR (CDCl$_3$ solution): $\delta$=5.7–5.3 (2H, m), 4.75–4.4 (2H, m), 3.66 (3H, s), 4.3–3.25 (7H, m), 1.05–0.7 (6H, m).

The following compounds were prepared by the same procedure as described above.

(a) (13E)-(9α,11α,15S,17S)-6-Oxo-9-hydroxy-11,15-bis(tetrahydropyran-2-yloxy)-17-methylprost-13-enoic acid methyl ester, having the following physical characteristics, was prepared from (13E)-(5RS,6RS,9α,1-1α,15S,17S)-5-bromo-6,9-epoxy-11,15-bis(tetrahydropyran-2-yloxy)-17-methylprost-13-enoic acid methyl ester [prepared as described in Reference Example 1(b)].

TLC (developing solvent, cyclohexane:ethyl acetate=2:1).

Rf=0.21.

IR (liquid film): $\nu$=2950, 2870, 1740, 1720, 980 cm$^{-1}$.

NMR (CDCl$_3$ solution): $\delta$=5.72–5.25 (2H, m), 4.77–4.50 (3H, m), 3.675 and 3.657 (3H, each s), 1.00–0.75 (6H, m).

(b) (13E)-(9α,11α,15R)-6-Oxo-9-hydroxy-11,15-bis(tetrahydropyran-2-yloxy)-16-(3-chlorophenoxy)-17,18,19,20-tetranoprost-13-enoic acid methyl ester, having the following physical characteristics, was prepared from (13E)-(5RS,6RS,9α,11α,15R)-5-iodo-6,9-epoxy-11,15-bis(tetrahydropyran-2-yloxy)-16-(3-chlorophenoxy)-17,18,19,20-tetranorprost-13-enoic acid methyl ester [prepared as described in Reference Example 2(a)].

TLC (developing solvent, cyclohexane:ethyl acetate=2:1).

Rf=0.15.

IR (liquid film): $\nu$=2945, 1740, 1720, 1590, 1580 cm$^{-1}$.

NMR (CDCl$_3$ solution): $\delta$=7.38–6.70 (4H, m), 5.75–5.46 (2H, m), 3.67 and 3.66 (3H, each s).

(c) (13E)-(9α,11α,15S)-6-Oxo-9-hydroxy-11,15-bis(tetrahydropyran-2-yloxy)-15-(3-butylcyclopentyl)-16,17,18,19,20-pentanorprost-13-enoic acid methyl ester, having the following physical characteristics, was prepared from (13E)-(5RS,6RS,9α,11α,15S)-5-iodo-6,9-epoxy-11,15-bis(tetrahydropyran-2-yloxy)-15-(3-butylcylopentyl)-16,17,18,19,20-pentanorprost-13-enoic acid methyl ester [prepared as described in Reference Example 2(b)].

TLC (developing solvent, cyclohexane:ethyl acetate=1:1).

Rf=0.46.

IR (liquid film): $\nu$=3450, 2950, 2860, 1745, 1730, 1470, 1450, 1440 cm$^{-1}$.

NMR (CDCl$_3$ solution): $\delta$=5.8–5.2 (2H, m), 4.8–4.5 (2H, m), 4.3–3.3 (7H, m), 3.665 and 3.660 (3H, each s), 2.7–1.0 (41H, m), 1.0–0.7 (3H, t).

(d) (13E)-(9α,11α,15RS)-6-Oxo-9-hydroxy-11,15-bis(tetrahydropyran-2-yloxy)-15-methylprost-13-enoic acid methyl ester, having the following physical characteristics, was prepared from (13E)-(5RS,6RS,9α,1-1α,15RS)-5-iodo-6,9-epoxy-11,15-bis(tetrahydropyran-2-yloxy)-15-methylprost-13-enoic acid methyl ester (prepared as described in Reference Example 3).

TLC (developing solvent, cyclohexane:ethyl acetate=1:1).

Rf=0.358.

IR (liquid film): $\nu$=2950, 2880, 1750, 1720, 1630 cm$^{-1}$.

NMR (CDCl$_3$ solution): $\delta$=5.65–5.35 (2H, m), 4.8–4.5 (2H, m), 3.67 (3H, s).

(e) (13E)-(9α,11α,15S,17S)-6-Oxo-9-hydroxy-11,15-bis(tetrahydropyran-2-yloxy)-17,20-dimethylprost-13-enoic acid methyl ester, having the following physical characteristics, was prepared from (13E)-(5RS,6RS,9α,11α,15S,17S)-5-iodo-6,9-epoxy-11,15-bis(tetrahydropyran-2-yloxy)-17,20-dimethylprost-13-enoic acid methyl ester [prepared as described in Reference Example 3(a)].

TLC (developing solvent, cyclohexane:ethyl acetate=1:1).

Rf=0.33.

IR (liquid film): $\nu$=2950, 2880, 1745 cm$^{-1}$.

NMR (CDCl$_3$ solution): $\delta$=5.51–5.15 (2H, m), 4.66–4.36 (2H, m), 3.51 (3H, s).

(f) (13E)-(9α,11α,15S,17S)-6-Oxo-9-hydroxy-11,15-bis(tetrahydropyran-2-yloxy)-17-methyl-20-ethylprost-13-enoic acid methyl ester, having the following physical characteristics, was prepared from (13E)-(5RS,6RS,9α,11α,15S,17S)-5-iodo-6,9-epoxy-11,15-bis(tetrahydropyran-2-yloxy)-17-methyl-20-ethylprost-13-enoic acid methyl ester [prepared as described in Reference Example 3(b)].

TLC (developing solvent, cyclohexane:ethyl acetate=1:1).

Rf=0.30.

IR (liquid film): $\nu$=2950, 2880, 1750 cm$^{-1}$.

NMR (CDCl$_3$ solution): $\delta$=5.4–5.21 (2H, m), 4.66–4.36 (2H, m), 3.54 (3H, s).

(g) (13E)-(9α,11α,15S)-6-Oxo-9-hydroxy-11,15-bis(tetrahydropyran-2-yloxy)-15-(4-propylcyclohexyl)-16,17,18,19,20-pentanorprost-13-enoic acid methyl ester, having the following physical characteristics, was prepared from (13E)-(5RS,6RS,9α,11α,15S)-5-iodo-6,9-epoxy-11,15-bis(tetrahydropyran-2-yloxy)-15-(4-propylcyclohexyl)-16,17,18,19,20-pentanorprost-13-enoic acid methyl ester [prepared as described in Reference Example 3(c)].

TLC (developing solvent, cyclohexane:ethyl acetate=1:1).

Rf=0.21.

IR (liquid film): $\nu$=2950, 2870, 1745 cm$^{-1}$.

NMR (CDCl$_3$ solution): $\delta$=5.48–5.2 (2H, m), 4.7–4.45 (2H, m), 3.54 (3H, s).

(h) (13E)-(9α,11α,15S)-2-Phenylseleno-6-oxo-9-hydroxy-11,15-bis(tetrahydropyran-2-yloxy)prost-13-enoic acid methyl ester, having the following physical characteristics, was prepared from (13E)-(5RS,6RS,9α,11α,15S)-2-phenylseleno-5-bromo-6,9-epoxy-11,15-bis(tetrahydropyran-2-yloxy)prost-13-enoic acid methyl ester (prepared as described in Reference Example 4).

TLC (developing solvent, cyclohexane:ethyl acetate=1:1).

Rf=0.42.

IR (liquid film): $\nu$=3450, 1740, 1720, 1580, 1440, 980 cm$^{-1}$.

NMR (CDCl$_3$ solution): $\delta$=7.7–7.4 (2H, m), 7.4–7.1 (3H, m), 4.8–4.4 (2H, m), 4.3–3.2 (8H, m), 3.62 (3H, s), 1.0–0.6 (3H, m).

REFERENCE EXAMPLE 9

(13E)-(9α,11α,15S)-6-Oxo-9-hydroxy-11,15-bis(tetrahydropyran-2-yloxy)-15-(3-propylcyclopentyl)-16,17,18,19,20-pentanorprost-13-enoic acid methyl ester Under an atmosphere of nitrogen, 7 ml of 50% aqueous acetic acid was added dropwise to a solution of 743 mg of (5Z,13E)-(9α,11α,15S)-6,9-epoxy-11,15-bis(tetrahydropyran-2-yloxy)-15-(3-propylcyclopentyl)-16,17,18,19,20-pentanorprosta-5,13-dienoic acid methyl ester (prepared as described in Reference Example 5) in 15 ml of tetrahydrofuran at room temperature and the mixture was stirred for 40 minutes. To the mixture thus obtained were added 3 g of sodium bicarbonate and 30 ml of water and the reaction mixture was extracted with diethyl ether. The extract was washed with an aqueous solution of sodium bicarbonate, dried over magnesium sulphate and concentrated under reduced pressure. The residue was purified by column chromatography on silica gel using a mixture of cyclohexane and ethyl acetate (1:1) as eluent to give 678 mg of the title compound having the following physical characteristics:

TLC (developing solvent, cyclohexane:ethyl acetate=2:1).

Rf=0.18.

IR (liquid film): $\nu$=2945, 2860, 1740, 1715 cm$^{-1}$.

NMR (CDCl$_3$ solution): $\delta$=5.58–5.28 (2H, m), 4.77–4.53 (2H, m), 3.66 and 3.65 (3H, each s), 0.99–0.76 (3H, m).

The following compound was prepared by the same procedure as described above.

(a) (13E)-(9α,11α,15S)-6-Oxo-9-hydroxy-11,15-bis(tetrahydropyran-2-yloxy)-15-(3-propylcyclopentyl)-16,17,18,19,20-pentanorprost-13-enoic acid was prepared from (5Z,13E)-(9α,11α,15S)-6,9-epoxy-11,15-bis(tetrahydropyran-2-yloxy)-15-(3-propylcyclopentyl)-16,17,18,19,20-pentanorprosta-5,13-dienoic acid (prepared as described in Reference Example 6). The compound thus obtained was used immediately in the next reaction [described in Example 1(j) hereafter].

REFERENCE EXAMPLE 10

(2E,13E)-(9α,11α,15S)-6-Oxo-9-hydroxy-11,15-bis(tetrahydropyran-2-yloxy)-prosta-2,13-dienoic acid methyl ester To a solution of 2.333 g of (13E)-(9α,11α,15S)-2-phenylseleno-6-oxo-9-hydroxy-11,15-bis(tetrahydropyran-2-yloxy)prost-13-enoic acid methyl ester [prepared as described in Reference Example 8(h)] in a mixture of 22 ml of ethyl acetate and 11 ml of tetrahydrofuran were added 733 mg of sodium bicarbonate and 1 ml of 30% (v/v) hydrogen peroxide at 34° C. and the mixture was stirred at that temperature for 30 minutes. The reaction mixture was then diluted with ethyl acetate, washed with water, an aqueous solution of sodium sulphate, water, an aqueous solution of ammonium chloride and an aqueous solution of sodium chloride, dried over magnesium sulphate and concentrated under reduced pressure. The residue was purified by column chromatography on silica gel using a mixture of cyclohexane and ethyl acetate (2:1) as eluent to give 1.524 g of the title compound having the following physical characteristics:

TLC (developing solvent, benzene:ethyl acetate=2:1).

Rf=0.20.

IR (liquid film): $\nu$=3400, 1730, 1660, 1440, 980 cm$^{-1}$.

NMR (CDCl$_3$ solution): $\delta$=7.2–6.7 (1H, m), 6.0–5.3 (3H, m), 4.8–4.5 (2H, m), 3.715 and 3.705 (3H, each s), 4.3–3.25 (7H, m), 1.05–0.7 (3H, m).

EXAMPLE 1

(13E)-(11α,15S)-6,9-Dioxo-11,15-bis(tetrahydropyran-2-yloxy)prost-13-enoic acid methyl ester To a solution of crude (13E)-(9α,11α,15S)-6-oxo-9-hydroxy-11,15-bis(tetrahydropyran-2-yloxy)prost-13-enoic acid methyl ester (prepared as described in Reference Example 7) in 10 ml of diethyl ether was added 10 ml of a chromic acid solution (obtained from 760 mg of chromium trioxide, 2.56 g of manganese sulphate, 0.84 ml of sulphuric acid and 19 ml of water) at 0° to 5° C., and the mixture was stirred at the same temperature for 1 hour. The reaction mixture was extracted with diethyl ether and the extract was washed with an aqueous solution of sodium bicarbonate and an aqueous solution of sodium chloride, dried over magnesium sulphate and concentrated under reduced pressure. The residue was purified by column chromatography on silica gel using a mixture of n-hexane and ethyl acetate (17:3) as eluent to give 480 mg of the title compound having the following physical characteristic:

TLC (developing solvent, ethyl acetate:n-hexane=1:1).

Rf=0.45.

The following compounds were prepared by the same procedure as described above.

(a) (13E)-(11α,15S,16S)-6,9-Dioxo-11,15-bis(tetrahydropyran-2-yloxy)-16-methylprost-13-enoic acid methyl ester, having the following physical characteristics, was prepared from (13E)-(9α,11α,15S,16S)-6-oxo-9-hydroxy-11,15-bis(tetrahydropyran-2-yloxy)-16-methylprost-13-enoic acid methyl ester (prepared as described in Reference Example 8).

TLC (developing solvent, cyclohexane:ethyl acetate=1:1).

Rf=0.30.

IR (liquid film): $\nu$=1740, 1710, 970 cm$^{-1}$.

(b) (13E)-(11α,15S,17S)-6,9-Dioxo-11,15-bis(tetrahydropyran-2-yloxy)-17-methylprost-13-enoic acid methyl ester, having the following physical characteristics, was prepared from (13E)-(9α,11α,15S,17S)-6-oxo-9-hydroxy-11,15-bis(tetrahydropyran-2-yloxy)-17-methylprost-13-enoic acid methyl ester [prepared as described in Reference Example 8(a)].

TLC (developing solvent, cyclohexane:ethyl acetate=2:1).

Rf=0.38.

IR (liquid film): $\nu$=2950, 2870, 1745, 1720, 970 cm$^{-1}$.

NMR (CDCl$_3$ solution): $\delta$=5.65–5.39 (2H, m), 4.76–4.50 (2H, m), 3.66 (3H, s), 0.98–0.79 (6H, m).

(c) (13E)-(11α,15R)-6,9-Dioxo-11,15-bis(tetrahydropyran-2-yloxy)-16-(3-chlorophenoxy)-17,18,19,20-tetranorprost-13-enoic acid methyl ester, having the following physical characteristics was prepared from (13E)-(9α,11α,15R)-6-oxo-9-hydroxy-11,15-bis(tetrahydropyran-2-yloxy)-16-(3-chlorophenoxy)-17,18,19,20-tetranorprost-13-enoic acid methyl ester [prepared as described in Reference Example 8(b)].

TLC (developing solvent, cyclohexane:ethyl acetate=2:1).

RF=0.31.

IR (liquid film): $\nu$=1750, 1720, 1590, 1580 cm$^{-1}$.

NMR (CDCl$_3$ solution): $\delta$=7.30–6.56 (4H, m), 5.83–5.47 (2H, m), 4.90–4.56 (2H, m), 3.58 (3H, s).

(d) (13E)-(11α,15S)-6,9-Dioxo-11,15-bis(tetrahydropyran-2-yloxy)-15-(3-butylcyclopentyl)-16,17,18,19,20-pentanorprost-13-enoic acid methyl ester, having the following physical characteristic, was prepared from (13E)-(9α,11α,15S)-6-oxo-9-hydroxy-11,15-bis(tetrahydropyran-2-yloxy)-15-(3-butylcyclopentyl)-16,17,18,19,20-pentanorprost-13-enoic acid methyl ester [prepared as described in Reference Example 8(c)].

TLC (developing solvent, cyclohexane:ethyl acetate=2:1).

Rf=0.34.

(e) (13E)-(11α,15RS)-6,9-Dioxo-11,15-bis(tetrahydropyran-2-yloxy)-15-methylprost-13-enoic acid methyl ester, having the following physical characteristic, was prepared from (13E)-(9α,11α,15RS)-6-oxo-9-hydroxy-11,15-bis(tetrahydropyran-2-yloxy)-15-methylprost-13-enoic acid methyl ester [prepared as described in Reference Example 8(d)].

TLC (developing solvent, benzene:ethyl acetate=1:1).

Rf=0.55.

(f) (13E)-(11α,15S,17S)-6,9-Dioxo-11,15-bis(tetrahydropyran-2-yloxy)-17,20-dimethylprost-13-enoic acid methyl ester, having the following physical characteristics, was prepared from (13E)-(9α,11α,15S,17S)-6-oxo-9-hydroxy-11,15-bis(tetrahydropyran-2-yloxy)-17,20-dimethylprost-13-enoic acid methyl ester [prepared as described in Reference Example 8(e)].

TLC (developing solvent, cyclohexane:ethyl acetate=2:1).

Rf=0.39.

IR (liquid film): ν=2950, 2880, 1750, 1720 cm$^{-1}$.

NMR (CDCl$_3$ solution): δ=5.6–5.21 (2H, m), 4.66–4.45 (2H, m), 3.51 (3H, s).

(g) (13E)-(11α,15S,17S)-6,9-Dioxo-11,15-bis(tetrahydropyran-2-yloxy)-17-methyl-20-ethylprost-13-enoic acid methyl ester, having the following physical characteristics, was prepared from (13E)-(9α,11α,15S,17S)-6-oxo-9-hydroxy-11,15-bis(tetrahydropyran-2-yloxy)-17-methyl-20-ethylprost-13-enoic acid methyl ester [prepared as described in Reference Example 8(f)].

TLC (developing solvent, cyclohexane:ethyl acetate=1:1).

Rf=0.43.

IR (liquid film): ν=2970, 2950, 2880, 1750, 1720, 1670, 1635 cm$^{-1}$.

NMR (CDCl$_3$ solution): δ=7.0–5.8 (2H, m), 5.2–4.6 (2H, m), 3.6 (3H, s).

(h) (13E)-(11α,15S)-6,9-Dioxo-11,15-bis(tetrahydropyran-2-yloxy)-15-(4-propylcyclohexyl)-16,17,18,19,20-pentanorprost-13-enoic acid methyl ester, having the following physical characteristics, was prepared from (13E)-(9α,11α,15S)-6-oxo-9-hydroxy-11,15-bis(tetrahydropyran-2-yloxy)-15-(4-propylcyclohexyl)-16,17,18,19,20-pentanorprost-13-enoic acid methyl ester [prepared as described in Reference Example 8(g)].

TLC (developing solvent, cyclohexane:ethyl acetate=1:1).

Rf=0.40.

IR (liquid film): ν=2880, 1750, 1720 cm$^{-1}$.

NMR (CDCl$_3$ solution): δ=5.54–5.24 (2H, m), 4.7–4.4 (2H, m), 3.54 (3H, s).

(i) (13E)-(11α,15S)-6,9-Dioxo-11,15-bis(tetrahydropyran-2-yloxy)-15-(3-propylcyclopentyl)-16,17,18,19,20-pentanorprost-13-enoic acid methyl ester, having the following physical characteristics, was prepared from (13E)-(9α,11α,15S)-6-oxo-9-hydroxy-11,15-bis(tetrahydropyran-2-yloxy)-15-(3-propylcyclopentyl)-16,17,18,19,20-pentanorprost-13-enoic acid methyl ester (prepared as described in Reference Example 9).

TLC (developing solvent, cyclohexane:ethyl acetate=2:1).

Rf=0.35.

IR (liquid film): ν=2935, 2855, 1743, 1718 cm$^{-1}$.

NMR (CDCl$_3$ solution): δ=5.63–5.26 (2H, m), 4.76–4.15 (2H, m), 3.63 (3H, s), 1.02–0.71 (3H, m).

(j) (13E)-(11α,15S)-6,9-Dioxo-11,15-bis(tetrahydropyran-2-yloxy)-15-(3-propylcyclopentyl)-16,17,18,19,20-pentanorprost-13-enoic acid, having the following physical characteristic, was prepared from (13E)-(9α,11α,15S)-6-oxo-9-hydroxy-11,15-bis(tetrahydropyran-2-yloxy)-15-(3-propylcyclopentyl)-16,17,18,19,20-pentanorprost-13-enoic acid [prepared as described in Reference Example 9(a)].

TLC (developing solvent, ethyl acetate): Rf=0.63.

(k) (2E,13E)-(11α,15S)-6,9-Dioxo-11,15-bis(tetrahydropyran-2-yloxy)prosta-2,13-dienoic acid methyl ester, having the following physical characteristics, was prepared from (2E,13E)-(9α,11α,15S)-6-oxo-9-hydroxy-11,15-bis(tetrahydropyran-2-yloxy)prosta-2,13-dienoic acid methyl ester (prepared as described in Reference Example 10).

TLC (developing solvent, benzene:ethyl acetate=2:1).

Rf=0.38.

IR (liquid film): ν=1750, 1725, 1660, 1440, 980 cm$^{-1}$.

EXAMPLE 2

(13E)-(11α,15S)-6,9-Dioxo-11,15-dihydroxyprost-13-enoic acid methyl ester (6-oxo-PGE$_1$ methyl ester)

To a solution of 480 mg of (13E)-(11α,15S)-6,9-dioxo-11,15-bis(tetrahydropyran-2-yloxy)prost-13-enoic acid methyl ester (prepared as described in Example 1) in 1 ml of tetrahydrofuran was added 3 ml of 65% (v/v) aqueous acetic acid and the mixture was stirred at 45° C. for 3 hours. The reaction mixture was diluted with 16 ml of water and extracted with a mixture of ethyl acetate and n-hexane (1:1). The extract was washed with water, an aqueous solution of sodium bicarbonate and an aqueous solution of sodium chloride, dried over magnesium sulphate and concentrated under reduced pressure. The residue was purified by column chromatography on silica gel using a mixture of ethyl acetate and n-hexane (1:1) as eluent to give 177 mg of the title compound having the following physical characteristics:

TLC (developing solvent, ethyl acetate): Rf=0.32.

IR (liquid film): ν=3630–3510, 1740, 1723, 1440, 1372, 1242, 1178, 1160, 1078, 975 cm$^{-1}$.

NMR (CDCl$_3$ solution): δ=5.65–5.40 (2H, m), 4.28–3.85 (2H, m), 3.65 (3H, s), 2.93–2.05 (10H, m), 1.00–0.75 (3H, m).

The following compounds were prepared by the same procedure as described above.

(a) (13E)-(11α,15S,16S)-6,9-Dioxo-11,15-dihydroxy-16-methylprost-13-enoic acid methyl ester [6-oxo-16S-methyl-PGE$_1$ methyl ester], having the following physical characteristics, was prepared from (13E)-(11α,15S,16S)-6,9-dioxo-11,15-bis(tetrahydropyran-2-yloxy)-16-methylprost-13-enoic acid methyl ester [prepared as described in Example 1(a)].

TLC (developing solvent, chloroform:tetrahydrofuran:acetic acid=10:2:1): Rf=0.23.

IR (liquid film): ν=3400, 1740, 1710, 970 cm$^{-1}$.

NMR (CDCl$_3$ solution): δ=5.7–5.45 (2H, m), 4.3–3.8 (2H, m), 3.66 (3H, s), 1.05–0.7. (6H, m).

(b) (13E)-(11α,15S,17S)-6,9-Dioxo-11,15-dihydroxy-17-methylprost-13-enoic acid methyl ester [6-oxo-17S-methyl-PGE$_1$ methyl ester], having the following physical characteristics, was prepared from (13E)-(11α,15S,17S)-6,9-dioxo-11,15-bis(tetrahydropyran-2-yloxy)-17-methylprost-13-enoic acid methyl ester [prepared as described in Example 1(b)].

TLC (developing solvent, ethyl acetate): Rf=0.58.

IR (liquid film): ν=2965, 2930, 2880, 1740, 1715, 970 cm$^{-1}$.

NMR (CDCl$_3$ solution): δ=5.62–5.48 (2H, m), 4.30–3.95 (2H, m), 3.66 (3H, s), 1.00–0.76 (6H, m).

(c) (13E)-(11α,15R)-6,9-Dioxo-11,15-dihydroxy-16-(3-chlorophenoxy)-17,18,19,20-tetranorprost-13-enoic acid methyl ester [6-oxo-16-(3-chlorophenoxy)-17,18,19,20-tetranor-PGE$_1$ methyl ester], having the following physical characteristics, was prepared from (13E)-(11α,15R)-6,9-dioxo-11,15-bis(tetrahydropyran-2-yloxy)-16-(3-chlorophenoxy)-17,18,19,20-tetranorprost-13-enoic acid methyl ester [prepared as described in Example 1(c)].

TLC (developing solvent, ethyl acetate): Rf=0.42.

IR (liquid film): ν=2950, 2880, 1740, 1715, 1590, 1580 cm$^{-1}$.

NMR (CDCl$_3$ solution): δ=7.31–6.72 (4H, m), 5.82–5.66 (2H, m), 4.60–4.40 (1H, m), 4.30–3.85 (5H, m), 3.65 (3H, s), 2.98–2.15 (10H, m), 1.68–1.45 (4H, m).

(d) (13E)-(11α,15S)-6,9-Dioxo-11,15-dihydroxy-15-(3-butylcyclopentyl)-16,17,18,19,20-pentanorprost-13-enoic acid methyl ester [6-oxo-15-(3-butylcyclopentyl)-16,17,18,19,20-pentanor-PGE$_1$ methyl ester], having the following physical characteristics, was prepared from (13E)-(11α,15S)-6,9-dioxo-11,15-bis(tetrahydropyran-2-yloxy)-15-(3-butylcyclopentyl)-16,17,18,19,20-pentanorprost-13-enoic acid methyl ester [prepared as described in Example 1(d)].

TLC (developing solvent, ethyl acetate): Rf=0.45.

IR (CHCl$_3$ solution): ν=3400, 2950, 2850, 1745, 1720, 1440, 1225, 1080, 970 cm$^{-1}$.

NMR (CDCl$_3$ solution): δ=5.7–5.4 (2H, m), 4.3–3.5 (6H, m), 3.0–2.1 (11H, m), 2.1–1.0 (18H, m), 1.0–0.7 (3H, broad t).

(e) (13E)-(11α, 15RS)-6,9-Dioxo-11,15-dihydroxy-15-methylprost-13-enoic acid methyl ester [6-oxo-15RS-methyl-PGE$_1$ methyl ester], having the following physical characteristics, was prepared from (13E)-(11α,15RS)-6,9-dioxo-11,15-bis(tetrahydropyran-2-yloxy)-15-methylprost-13-enoic acid methyl ester [prepared as described in Example 1(e)].

TLC (developing solvent, chloroform:tetrahydrofuran: acetic acid=10:2:1): RF=0.25.

IR (liquid film): ν=2950, 2870, 1730, 1720, 1460, 1440, 1380 cm$^{-1}$.

NMR (CDCl$_3$ solution): δ=5.9–5.5 (2H, m), 4.3–3.9 (1H, m), 3.67 (3H, s), 1.28 (3H, s).

(f) (13E)-(11α,15S, 17S)-6,9-Dioxo-11,15-dihydroxy-17,20-dimethylprost-13-enoic acid methyl ester [6-oxo-17S,20-dimethyl-PGE$_1$ methyl ester], having the following physical characteristics, was prepared from (13E)-(11α,15S,17S)-6,9-dioxo-11,15-bis(tetrahydropyran-2-yloxy)-17,20-dimethylprost-13-enoic acid methyl ester [prepared as described in Example 1(f)].

TLC (developing solvent, ethyl acetate): Rf=0.39.

IR (liquid film): ν=2980, 2950, 2890, 1750, 1720, 1440 cm$^{-1}$.

NMR (CDCl$_3$ solution): δ=5.65–5.50 (2H, m), 4.3–3.9 (2H, m) 3.67 (3H, s), 1.0–0.7 (6H, m).

(g) (13E)-(11α,15S, 17S)-6,9-Dioxo-11,15-dihydroxy-17-methyl-20-ethylprost-13-enoic acid methyl ester [6-oxo-17S-methyl-20-ethyl-PGE$_1$ methyl ester], having the following physical characteristics, was prepared from (13E)-(11α,15S,17S)-6,9-dioxo-11,15-bis(tetrahydropyran-2-yloxy)-17-methyl-20-ethylprost-13-enoic acid methyl ester [prepared as described in Example 1(g)].

TLC (developing solvent, ethyl acetate): Rf=0.30.

IR (liquid film): ν=2970, 2950, 2870, 1745, 1720, 1440, 1380 cm$^{-1}$.

NMR (CDCl$_3$ solution): δ=5.65–5.50 (2H, m), 4.3–3.9 (2H, m), 3.66 (3H, s), 1.0–0.7 (6H, m).

(h) (13E)-(11α,15S)-6,9-Dioxo-11,15-dihydroxy-15-(4-propylcyclohexyl)-16,17,18,19,20-pentanorprost-13-enoic acid methyl ester [6-Oxo-15-(4-propylcyclohexyl)-16,17,18,19,20-pentanor-PGE$_1$ methyl ester], having the following physical characteristics, was prepared from (13E)-(11α,15S)-6,9-dioxo-11,15-bis(tetrahydropyran-2-yloxy)-15-(4-propylcyclohexyl)-16,17,18,19,20-pentanorprost-13-enoic acid methyl ester [prepared as described in Example 1(h)].

TLC (developing solvent, ethyl acetate): Rf=0.28.

IR (KBr tablet): ν=2970, 2950, 2880, 1750, 1735, 1720, 1385, 1360, 1260 cm$^{-1}$.

NMR (CDCl$_3$ solution): δ=5.7–5.5 (2H, m), 4.3–3.3 (4H, m), 3.68 (3H, s).

(i) (13E)-(11α,15S)-6,9-Dioxo-11,15-dihydroxy-15-(3-propylcyclopentyl)-16,17,18,19,20-pentanorprost-13-enoic acid methyl ester [6-oxo-15-(3-propylcyclopentyl)-16,17,18,19,20-pentanor-PGE$_1$ methyl ester], having the following physical characteristics, was prepared from (13E)-(11α,15S)-6,9-dioxo-11,15-bis(tetrahydropyran-2-yloxy)-15-(3-propylcyclopentyl)-16,17,18,19,20-pentanorprost-13-enoic acid methyl ester [prepared as described in Example 1(i)].

TLC (developing solvent, ethyl acetate): Rf=0.57.

IR (KBr tablet): ν=2950, 2870, 1745, 1725, 1710 cm$^{-1}$.

NMR (CDCl$_3$ solution): δ=5.67–5.47 (2H, m), 4.30–3.70 (4H, m), 3.66 (3H, s), 0.99–0.80 (3H, m).

(j) (13E)-(11α,15S)-6,9-Dioxo-11,15-dihydroxy-15-(3-propylcyclopentyl)-16,17,18,19,20-pentanorprost-13-enoic acid [6-oxo-15-(3-propylcyclopentyl)-16,17,18,19,20-pentanor-PGE$_1$], having the following physical characteristics, was prepared from (13E)-(11α,15S)-6,9-dioxo-11,15-bis(tetrahydropyran-2-yloxy)-15-(3-propylcyclopentyl)-16,17,18,19,20-pentanorprost-13-enoic acid [prepared as described in Example 1(j)].

TLC (developing solvent, ethyl acetate:formic acid=400:5).

Rf=0.38.

IR (CHCl$_3$ solution): ν=3450, 2950, 2870, 1750, 1720, 1450, 1430, 1250, 1160, 1080, 980 cm$^{-1}$.

NMR (CDCl$_3$ solution): δ=5.9–5.3 (5H, m), 4.3–4.0 (1H, m), 4.0–3.7 (1H, m), 3.0–2.2 (10H, m), 2.2–1.05 (16H, m), 1.05–0.7 (3H, broad t).

(k) (2E,13E)-(11α,15S)-6,9-Dioxo-11,15-dihydroxyprosta-2,13-dienoic acid methyl ester [6-oxo-trans-2,3-didehydro-PGE$_1$ methyl ester], having the following physical characteristics, was prepared from (2E,13E)-(11α,15S)-6,9-dioxo-11,15-bis(tetrahydropyran-2-yloxy)prosta-2,13-dienoic acid methyl ester [prepared as described in Example 1(k)].

TLC (developing solvent, chloroform:tetrahydrofuran:acetic acid=10:2:1): Rf=0.20.

IR (CHCl$_3$ solution): $\nu$=3400, 1745, 1720, 1660, 1440, 970 cm$^{-1}$.

NMR (CDCl$_3$ solution): $\delta$=7.1–6.7 (1H, m), 5.95–5.4 (3H, m), 4.3–3.85 (2H, m), 3.71 (3H, s), 1.05–0.7 (3H, m).

EXAMPLE 3

α-Cyclodextrin clathrate of 6-oxo-17S,20-dimethyl-PGE$_1$ methyl ester

A solution of 3.64 mg of 6-oxo-17S,20-dimethyl-PGE$_1$ methyl ester [prepared as described in Example 2(f)] in 0.6 ml of ethanol was added to a solution of 110.66 mg of α-cyclodextrin in 2 ml of water and the mixture was stirred at room temperature for 5 minutes. The mixture was concentrated under reduced pressure to give 98.22 mg of the α-cyclodextrin clathrate of the compound specified in the title. The content of 6-oxo-17S,20-dimethyl-PGE$_1$ methyl ester in the product was 3.2% by weight.

EXAMPLE 4

β-Cyclodextrin clathrate of 6-oxo-17S,20-dimethyl-PGE$_1$ methyl ester

A solution of 3.35 mg of 6-oxo-17S,20-dimethyl-PGE$_1$ methyl ester [prepared as described in Example 2(f)] in 0.6 ml of ethanol was added to a solution of 41.9 mg of δ-cyclodextrin in 2.1 ml of water and the mixture was stirred at room temperature for 5 minutes. The mixture was concentrated under reduced pressure to give 35.28 mg of the β-cyclodextrin clathrate of the compound specified in the title. The content of 6-oxo-17S,20-dimethyl-PGE$_1$ methyl ester in the product was 8.1% by weight.

The present invention includes within its scope pharmaceutical compositions which comprise at least one new therapeutically useful compound of general formula IV, or cyclodextrin clathrate thereof or, when R$^1$ in formula IV represents a hydrogen atom or a group —C$_m$H$_{2m}$COOR$^5$ in which R$^5$ represents a hydrogen atom and m is as hereinbefore defined, non-toxic salt thereof or, when R$^1$ represents a group

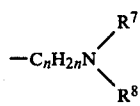

in which n, R$^7$ and R$^8$ are as hereinbefore defined, non-toxic acid addition salt thereof, together with a pharmaceutical carrier or coating. In clinical practice the new compounds of general formula IV will normally be administered orally, vaginally, rectally or parenterally.

Solid compositions for oral administration include compressed tablets, pills, dispersible powders, and granules. In such solid compositions one or more of the active compounds is, or are, admixed with at least one inert diluent such as calcium carbonate, potato starch, alginic acid, lactose or mannitol. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing one or more of the active substances with or without the addition of diluents or excipients.

Solid compositions for vaginal administration include pessaries formulated in manner known per se and containing one or more of the active compounds.

Solid compositions for rectal administration include suppositories formulated in manner known per se and containing one or more of the active compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment.

In the human adult, the doses per person are generally between 0.005 and 5 mg. by oral administration in the treatment of hypertension, between 0.005 and 5 mg. by oral administration in the treatment of disorders of the peripheral circulation, between 0.01 and 50 mg by oral administration in the prevention and treatment of cerebral thrombosis and myocardial infarction, between 0.0005 and 1 mg. by oral administration in the treatment of gastric ulceration, between 0.00005 and 5 mg. by oral, intravaginal, intrauterine, intravenous, intramuscular and extra-ovular administration in the termination of pregnancy and induction of labour in pregnant female mammals and in the treatment of impaired fertility, in the control of oestrus, contraception and menstrual regulation in female mammals. In domestic female mammals such as cows, mares, sows, ewes and bitches, the doses are generally between 0.01 and 50 mg/animal by intramuscular, subcutaneous, intrauterine, intravaginal and intravenous administration for the synchronisation of oestrus, treatment of impaired fertility and the induction of abortion and labour.

The following Example illustrates pharmaceutical compositions according to the invention.

EXAMPLE 5

6-Oxo-17S,20-dimethyl-PGE$_1$ methyl ester (2 mg) was dissolved in ethanol (10 ml), mixed with marnitol (18.5 g), sieved through a 30-mesh sieve, dried at 30° C. for 90 minutes and again sieved through a 30-mesh sieve. Aerosil (microfine silica, 200 mg) was added and the powder obtained was machine filled into one hundred No. 2 hard gelatin capsules to give capsules each containing 20 μ g of 6-oxo-17S,20-dimethyl-PGE₁ methyl ester, which after swallowing of the capsule is released into the stomach. "Aerosil" is a registered Trade Mark.

6-Oxo-17S,20-dimethyl-PGE₁ methyl ester (2 mg) was dissolved in ethanol (10 ml), mixed with marnitol (18.5 g), sieved through a 30-mesh sieve, dried at 30° C. for 90 minutes and again sieved through a 30-mesh sieve. Aerosil (microfine silica, 200 mg) was added and the powder obtained was machine filled into one hundred No. 2 hard gelatin capsules to give capsules each containing 20μ g of 6-oxo-17S,20-dimethyl-PGE₁ methyl ester, which after swallowing of the capsule is released into the stomach. "Aerosil" is a registered Trade Mark.

We claim:

1. A prostaglandin E₁ analogue of the general formula:

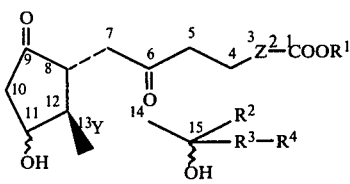
IV wherein Y represents trans-vinylene, Z represents ethylene, $R^1$ represents a hydrogen atom, a straight- or branched-chain alkyl group containing from 1 to 12 carbon atoms, an aralkyl group containing from 7 to 12 carbon atoms, a cycloalkyl group containing from 4 to 7 carbon atoms in the ring and unsubstituted or substituted by at least one straight- or branched-chain alkyl group containing from 1 to 6 carbon atoms, a phenyl group unsubstituted or substituted by at least one chlorine atom, trifluoromethyl group, straight- or branched-chain alkyl group containing from 1 to 4 carbon atoms or phenyl group, a —$C_mH_{2m}COOR^5$ group (wherein m represents an integer of from 1 to 12 and $R^5$ represents a hydrogen atom or a straight- or branched-chain alkyl group containing from 1 to 4 carbon atoms), a —$C_nH_{2n}OR^6$ group (wherein $R^6$ represents a hydrogen atom or a straight- or branched-chain alkyl group containing from 1 to 4 carbon atoms and n represents an integer of from 2 to 12) or a

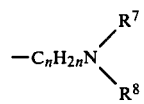

group (wherein $R^7$ and $R^8$, which may be the same or different, each represent a hydrogen atom or a straight- or branched-chain alkyl group containing from 1 to 4 carbon atoms and n is as hereinbefore defined), $R^2$ represents a hydrogen atom, $R^3$ and $R^4$ together represent 2-methylhexyl group, and the wavy line attached to the C-11 and C-15 carbon atoms represents α- or β-configuration or mixtures thereof and cyclodextrin clathrates of such acids and esters and, when $R^1$ represents a hydrogen atom or a group —$C_mH_{2m}COOR^5$ in which $R^5$ represents a hydrogen atom and m is as hereinbefore defined, non-toxic salts thereof and, when $R^1$ represents a group

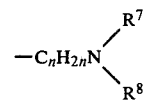

in which n, $R^7$ and $R^8$ are as hereinbefore defined, non-toxic acid addition salts thereof.

2. A prostaglandin analogue according to claim 1 wherein $R^1$ represents a hydrogen atom or a straight- or branched-chain alkyl group containing from 1 to 4 carbon atoms.

3. A prostaglandin analogue according to claim 1 wherein $R^1$ represents a hydrogen atom or a methyl group.

4. A prostaglandin analogue according to claim 1 wherein the hydroxy groups attached to the C-11 and C-15 atoms in general formula IV depicted in claim 1 are in α-configuration.

5. A prostaglandin analogue according to claim 1 which is (13E)-(11α,15S,17S)-6,9-dioxo-11,15-dihydroxy-17,20-dimethylprost-13-enoic acid methyl ester.

6. A prostaglandin analogue according to claim 1 which is an α-cyclodextrin clathrate of the prostaglandin analogue claimed in claim 5.

7. A prostaglandin analogue according to claim 1 which is a β-cyclodextrin clathrate of the prostaglandin analogue claimed in claim 5.

8. A pharmaceutical composition useful in the treatment of hypertension, in the treatment of disorders of the peripheral circulation, in the prevention and treatment of cerebral thrombosis and myocardial infarction, in the treatment of gastric ulceration, in the termination of pregnancy and induction of labour in pregnant female mammals, in the treatment of imparied fertility and in the control of oestrus, contraception and menstrual regulation in female mammals, which comprises, as active ingredient, an effective amount of at least one prostaglandin analogue as claimed in claim 1 or a cyclodextrin clathrate thereof or, when $R^1$ in general formula IV depicted in claim 1 represents a hydrogen atom or a group —$C_mH_{2m}COOR^5$ in which $R^5$ represents a hydrogen atom and m is as defined in claim 1, a non-toxic salt thereof or, when $R^1$ represents a group

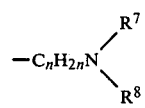

in which n, $R^7$ and $R^8$ are as defined in claim 1, a non-toxic acid addition salt thereof, in association with a pharmaceutical carrier or coating.

* * * * *